US011028362B2

(12) United States Patent
Ryzhuk et al.

(10) Patent No.: US 11,028,362 B2
(45) Date of Patent: Jun. 8, 2021

(54) DECELLULARIZED HUMAN AMNIOTIC MEMBRANE FOR CELL DELIVERY, CELL CULTURE AND INFLAMMATION PREVENTION

(71) Applicant: The Regents of the University of California, Oakland, CA (US)

(72) Inventors: Volodymyr Ryzhuk, Sacramento, CA (US); Aijun Wang, Sacramento, CA (US); Diana Farmer, Sacramento, CA (US); Benjamin Keller, Sacramento, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 348 days.

(21) Appl. No.: 15/567,058

(22) PCT Filed: Apr. 15, 2016

(86) PCT No.: PCT/US2016/027967
§ 371 (c)(1),
(2) Date: Oct. 16, 2017

(87) PCT Pub. No.: WO2016/168752
PCT Pub. Date: Oct. 20, 2016

(65) Prior Publication Data
US 2018/0100139 A1   Apr. 12, 2018

Related U.S. Application Data

(60) Provisional application No. 62/149,447, filed on Apr. 17, 2015.

(51) Int. Cl.
| *C12N 5/073* | (2010.01) |
| *A61K 35/50* | (2015.01) |
| *A61K 35/28* | (2015.01) |
| *C12N 5/071* | (2010.01) |
| *A61K 9/00* | (2006.01) |
| *A61K 35/39* | (2015.01) |
| *A61K 38/48* | (2006.01) |
| *C12N 5/0775* | (2010.01) |
| *A61L 27/38* | (2006.01) |
| *A61L 27/52* | (2006.01) |
| *A61L 26/00* | (2006.01) |
| *A61L 27/36* | (2006.01) |

(52) U.S. Cl.
CPC .......... *C12N 5/0605* (2013.01); *A61K 9/0019* (2013.01); *A61K 35/28* (2013.01); *A61K 35/39* (2013.01); *A61K 35/50* (2013.01); *A61K 38/488* (2013.01); *A61L 26/008* (2013.01); *A61L 26/0057* (2013.01); *A61L 27/3604* (2013.01); *A61L 27/3683* (2013.01); *A61L 27/3834* (2013.01); *A61L 27/52* (2013.01); *C12N 5/063* (2013.01); *C12N 5/0662* (2013.01); *C12N 5/0668* (2013.01); *A61L 2430/38* (2013.01); *C12N 2533/54* (2013.01); *C12N 2533/92* (2013.01)

(58) Field of Classification Search
None
See application file for complete search history.

(56) References Cited

U.S. PATENT DOCUMENTS

| 8,703,206 | B2 | 4/2014 | Daniel et al. | |
| 2003/0187515 | A1* | 10/2003 | Hariri | A61K 35/50 623/23.72 |
| 2011/0129590 | A1 | 6/2011 | Deibler et al. | |

FOREIGN PATENT DOCUMENTS

| CN | 1777437 A | 5/2006 | |
| CN | 104225667 A * | 12/2014 | ............. A61L 15/40 |
| EP | 0 686 402 A1 | 12/1995 | |
| WO | WO-2012/083023 A1 | 6/2012 | |
| WO | WO-2012/088396 A2 | 6/2012 | |
| WO | WO-2014/039429 A1 | 3/2014 | |
| WO | WO-2014/040026 A2 | 3/2014 | |

OTHER PUBLICATIONS

Chao et al CN104225667A , published Dec. 24, 2014 (machine translation), 27 pages. (Year: 2014).*
"Gel" Definition from Dictionary.com, https://www.dictionary.com/browse/gel; retrieved Feb. 3, 2020. (Year: 2020).*
"Hydrogel" Definition from Dictionary.com, https://www.dictionary.com/browse/hydrogel?s=t; retrieved Feb. 3, 2020. (Year: 2020).*
"Powder" Definition from Merriam-Webster Online Dictionary, https://www.merriam-webster.com/dictionary/powder; retrieved Feb. 4, 2020. (Year: 2020).*
Crapo et al, Biomaterials, 2011, vol. 32, pp. 3233-3243. (Year: 2011).*
Dow Surfactants Reference Chart, Form No. 119-01491-0120 S2D. 2020. Retrieved from URL: https://www.dow.com/content/dam/dcc/documents/en-us/catalog-selguide/119/119-01491-01-dow-surfactants-selection-guide.pdf?iframe=true (Year: 2020).*
International Preliminary Report on Patentability dated Oct. 26, 2017, from application No. PCT/US2016/027967.
International Search Report and Written Opinion dated Jul. 26, 2016, from application No. PCT/US2016/027967.
Beer, et al., "Expression and Function of Keratinocyte Growth Factor and Activin in Skin Morphogenesis and Cutaneous Wound Repair", J Investig Dermatol Symp Proc, vol. 5, No. 1, Dec. 2000, pp. 34-39.
Bollini, et al., "The Regenerative Role of the Fetal and Adult Stem Cell Secretome", Journal of Clinical Medicine, 2013, 2(4), pp. 302-327.

(Continued)

*Primary Examiner* — Allison M Fox
(74) *Attorney, Agent, or Firm* — Foley & Lardner LLP

(57) ABSTRACT

Provided herein is an isolated decelluarized amniotic membrane (DCM) and methods for using same therapeutically in vivo and in vitro. In one aspect, the isolated DCM is further processed, freezing, freeze drying, lyophilization micronized into powder or treatment with pepsin to create a hydrogel.

25 Claims, 10 Drawing Sheets

(56) References Cited

OTHER PUBLICATIONS

Brown, et al., "The Basement Membrane Component of Biologic Scaffolds Derived from Extracellular Matrix", Tissue Engineering, vol. 12, No. 3, 2006, pp. 519-526.
Caplan, et al., "Mesenchymal Stem Cells as Trophic Mediators", Journal of Cellular Biochemistry, 2006, 98(5),pp. 1076-1084.
Clark, et al., "Tissue Engineering for Cutaneous Wounds", Journal of Investigative Dermatology, 2007, 127(5), pp. 1018-1029.
Davis, et al., "Enhancing Osteoconductivity of Fibrin Gels with Apatite-Coated Polymer Microspheres", Tissue Engineering: Part A, vol. 19, Nos. 15 and 16, 2013, pp. 1773-1782.
DeQuach, et al., "Simple and High Yielding Method for Preparing Tissue Specific Extracellular Matrix Coatings for Cell Culture", PLoS One, Sep. 2010, vol. 5, Issue 9.
Diegelmann, et al., "Wound Healing: An Overview of Acute, Fibrotic and Delayed Healing", Frontiers in Bioscience, 9(1), pp. 283-289, Jan. 1, 2004.
Dominici, et al., "Minimal criteria for defining multipotent mesenchymal stromal cells. The International Society for Cellular Therapy position statement", Cytotherapy, 2006, vol. 8, No. 4, pp. 315-317.
Donnelly, et al., "A Novel Bioreactor for Stimulating Skeletal Muscle In Vitro", Tissue Engineering: Part C, 2010, vol. 16, No. 4, pp. 711-718.
Elgharably, et al., "A Modified Collagen Gel Enhances Healing Outcome in a Pre-Clinical Swine Model of Excisional Wounds", Wound Repair and Regeneration, May 2013, 21(3), pp. 473-481.
Firth, et al., "Cellular Actions of the Insulin-Like Growth Factor Binding Proteins", Endocrine Reviews, 2002, 23(6), pp. 824-854.
Gholipourmalekabadi, et al., "Development of a Cost-Effective and Simple Protocol for Decellularization and Preservation of Human Amniotic Membrane as a Soft Tissue Replacement and Delivery System for Bone Marrow Stromal Cells, Advanced Healthcare Materials", 2015.
Gupta, et al, "A potent inhibitor of endothelial cell proliferation is generated by proteolytic cleavage of the chemokine platelet factor 4", Proc. Natl. Acad. Sci., Aug. 1995, vol. 92, pp. 7799-7803.
Hao, et al., "Identification of Antiangiogenic and Antiinflammatory Proteins in Human Amniotic Membrane", Cornea, 2000, 19(3). pp. 348-352.
Huang, et al, "The Modulation of Endothelial Cell Morphology, Function, and Survival Using Anisotropic Nanofibrillar Collagen Scaffolds", Biomaterials, May 2013, 34(16), pp. 4038-4047.
Huh, et al, "From 3D cell culture to organs-onchips", Trends in cell biology, 2011, 21(12), pp. 745-754.
Karp, et al., "Mesenchymal Stem Cell Homing: The Devil Is in the Details", Cell Stem Cell, 2009, 4(3), 206-216.
Kim, et al., "Fibrin Glue Improves the Therapeutic Effect of MSCs by Sustaining Survival and Paracrine Function", Tissue Engineering: Part A, 2013, vol. 19, Nos. 21 and 22, pp. 2373-2381.
Koizumi, et al., "Growth factor mRNA and protein in preserved human amniotic membrane" Current Eye Research, 2000, vol. 20, No. 3, pp. 173-177.
Lankford, L. et al., "Early gestation chorionic villi-derived stromal cells for fetal tissue engineering", World Journal of Stem Cells, Jan. 26, 2015, 7(1), pp. 195-207.
Li, et al., "IL-8 Directly Enhanced Endothelial Cell Survival, Proliferation, and Matrix Metalloproteinases Production and Regulated Angiogenesis", The Journal of Immunology, 2003, 170(6), pp. 3369-3376.
Malek, et al., "Human Placental Stem Cells: Biomedical Potential and Clinical Relevance", Journal of Stem Cells, 2011, vol. 6, No. 2, pp. 75-92.
Malhotra, et al., "Human amniotic membrane transplantation: Different modalities of its use in ophthalmology", World Journal of Transplantation, Jun. 24, 2014, 4(2), pp. 111-121.
Manuelpillai, et al., "Amniotic membrane and amniotic cells: Potential therapeutic tools to combat tissue inflammation and fibrosis?", Placenta, 2011, 32 Suppl 4, S320-325.
Meierhenry, et al., "Placenta as a Source of Stem Cells for Regenerative Medicine", Current Pathobiology Reports, 2015, 3(1), pp. 9-16.
Murphy, et al., "Mesenchymal stem cells: environmentally responsive therapeutics for regenerative medicine", Experimental & Molecular Medicine, 2013, 45, e54.
Orban, et al. "Crosslinking of collagen gels by transglutaminase", Journal of Biomedical Materials Research Part A, Mar. 2004, 68(4), pp. 756-762.
Parolini, et al., "Review: Preclinical studies on placenta-derived cells and amniotic membrane: An update", Placenta, 2011, 32(Suppl 2):S186-S195.
Phinney, et al., Concise Review: Mesenchymal Stem/Multipotent Stromal Cells: The State of Transdifferentiation and Modes of Tissue Repair—Current Views, Stem Cells, 2007, 25(11), pp. 2896-2902.
Rahman, et al., "Amniotic membrane in ophthalmology: indications and limitations", Eye, 2009, 23, pp. 1954-1961.
Roy, et al., "Processing of Type I Collagen Gels Using Non-Enzymatic Glycation", J Biomed Mater Res A, Jun. 1, 2010, 93(3), pp. 843-851.
Slaughter, et al., "Hydrogels in Regenerative Medicine", Advanced Materials, Sep. 4, 2009, 21(0), pp. 3307-3329.
van Hinsbergh, et al., "Endothelial sprouting and angiogenesis: matrix metalloproteinases in the lead", Cardiovascular Research, 2008, 78, pp. 203-212.
Wolf, et al., "A Hydrogel Derived From Decellularized Dermal Extracellular Matrix", Biomaterials, Oct. 3, 2012, 33(29), pp. 7028-7038.
Ballios, et al., "A hydrogel-based stem cell delivery system to treat retinal degenerative diseases", Biomaterials, vol. 31, Jan. 6, 2010, pp. 2555-2564.
Catelas, et al., "Human Mesenchymal Stem Cell Proliferation and Osteogenic Differentiation in Fibrin Gels in Vitro", Tissue Engineering, vol. 12, No. 8, 2006, pp. 2385-2396.
Hoeben, et al., "Vascular Endothelial Growth Factor and Angiogenesis", Pharmacological Reviews, vol. 56, No. 4, 2004, pp. 549-580.
Luttun, et al., "Placental Growth Factor (PlGF) and Its Receptor Flt-1 (VEGFR-1) Novel Therapeutic Targets for Angiogenic Disorders", 979, 2002, pp. 80-93.
Midwood, et al., "Tissue repair and the dynamics of the extracellular matrix", The International Journal of Biochemistry & Cell Biology, vol. 36, 2004, pp. 1031-1037.

* cited by examiner

DECELLULARIZED HUMAN AMNIOTIC MEMBRANE FOR CELL DELIVERY, CELL CULTURE AND INFLAMMATION PREVENTION

CROSS-REFERENCE TO RELATED APPLICATION

This application is a National Stage Entry of International Application No. PCT/US2016/027967, filed Apr. 15, 2016, which claims the benefit of the filing date of U.S. Provisional Patent Application No. 62/149,447, filed Apr. 17, 2015. The foregoing are incorporated by reference herein in their entireties.

BACKGROUND

Over the past two decades, there has been increased interest in the decellularization of tissues and organs to create biologic extracellular matrix scaffolds. These scaffolds contain the microstructure of the native tissue, which can, in theory, provide the framework for tissue and organ regeneration when seeded with stem cells. The exciting potential around decellularized tissues has resulted in researchers investigating decellularization of several tissues including skin, small intestinal submucosa, bladder, blood vessels, heart valves, and liver (Chen, R. N. et al. (2004) Biomaterials 25:2679-2686; Badylak, S. F. et al. (1995) Journal of Biomedical Materials Research 29:977-985; Chen, F. et al. (1999) Urology 54:407-410; Dahl, S. L. et al. (2003) Cell Transplantation 12:659-666; Korossis, S. A. et al. (2002) The Journal of Heart Valve Disease 11:463-471; Uygun, B. E. et al. (2010) Nature Medicine 16:814-820). These decellularized scaffolds have been successfully in several clinical applications including skin and bone grafting, dural repair, hernia and tendon repair tendon repair, and heart valve replacement. While several research groups have attempted to recelluarize and entire organ, the ultimate goal of creating an "off-the-shelf" organ has not yet been achieve.

SUMMARY

While a few groups have investigated decellularization of the placenta, the full clinical potential of placental decellularization has not yet been established. The placenta is a unique organ has not yet been a major focus of decellularization and Applicants believe the unique regenerative properties of the placenta could present unique advantages over other decellularized tissues for stem cell delivery, tissue engineering, wound healing and inflammation prevention.

As provided in more detail below, term placenta is utilized and the amniotic membrane is harvested and the cellular component is removed using a standard protocol. This results in a decelluarized amniotic membrane sheet which can then be used to create an amnionin-derived extracellular matrix hydrogel, or to be micronized into powder that can be administered as a topic powder or mixed with saline to create an injectable, flowable matrix solution or a topical gel. These decelluarized products can be used for stem cell delivery, cell culture and for inflammation prevention such as for peritoneal adhesion application. The creation of decelluarized amnion and the derivatives and the utilization of these products to prevent adhesion and scar formation, such as applications for healing wounds, regenerating tissues and preventing adhesions, have novel therapeutic potential.

In one aspect provided herein is an isolated decelluarized amniotic membrane (DCM) that can be isolated from any appropriate source, e.g., a human, a bovine, an equine, a feline, a canine or a murine. In a further aspect, the isolated DCM is processed by freezing, freeze drying, lyophilization and/or micronized into powder or treatment with pepsin to create a hydrogel. In a further aspect the DCM or the processed product is combined with a carrier, e.g., a pharmaceutically acceptable carrier, e.g., one or more of phosphate buffered saline, deionized water, a hydrogel or a collagen-based product.

The above compositions can further comprise, or alternatively consist essentially of, or yet further consist of, one or more therapeutic cell. Non-limiting examples of such cells include a stem cell, e.g., a mesenchymal stem cell. The cell can be from the same species of the isolated DCM or another species as appropriate.

Also provided herein is a method to culture a cell, comprising, or alternatively consisting essentially of, or yet further consisting of, mixing the cell with the isolated DCM with a hydrogel or collagen-based product and culturing the cell in the combined composition under conditions that favor growth and expansion of the cell. The mixing can be performed in vitro or in vivo. In one aspect the cell is a therapeutic cell, e.g., a stem cell, such as a mesenchymal stem cell.

Therapeutic methods also are provided. A method to treat a wound is provided by administering to a subject in need thereof, an effective amount the isolated DCM as described above or other composition as described above. A method for regulating, treating or preventing inflammation in a subject in need thereof is further provided by administering to the subject in need thereof, an effective amount the isolated DCM as described above or other composition as described above. Further provided is a method for treating or preventing adhesion or scar formation in a subject in need thereof, by administering to the subject in need thereof, an effective amount of the isolated DCM as described above or other composition as described above. A method to treat spinal cord injury or Spina *bifida* is provided by administering to a subject in need thereof an effective amount of the isolated DCM as described above or other composition as described above. Yet further provided is a method to promote vascularization in a subject in need thereof, by administering to the subject an effective amount of isolated DCM as described above or other composition as described above. In one aspect, the compositions further comprise stem cells, that may be allogeneic or autologous to the subject being treated.

The methods can be used therapeutically to treat a human patient or to treat an animal, e.g., a bovine, an equine, a feline, a canine or a murine.

Also provided is a kit containing a composition as described above and optionally instructions for use.

The compositions as described herein can be used to treat spinal cord injury and Spina *bifida*. Therapeutic compositions as described herein, and derived from human placenta for use in humans, can be administered in vivo and in utero, as necessary.

The compositions as described herein can be modified to optimize its various immunomodulatory properties and administered in an effective amount to a patient or subject in need of such therapy.

The compositions as described herein can be used to differentiate stem cells in vitro and in vivo into various tissue lineages. Cells and tissue can be derived from pluripotent stem cells or harvested from tissues such as bone marrow, adipose tissue, lungs, tooth buds, for use as noted herein.

Therapeutic effects exerted by the compositions as described herein are likely due to the biologically functional biomolecules contained such as extracellular matrices, cytokines, chemokines, prostaglandins, etc. Thus, the compositions as described herein can be administered to a subject or patient in need thereof to regulate inflammation and promote vascularization.

BRIEF DESCRIPTION OF THE DRAWINGS

(FIG. 1A) Hydrogel with concentration of 3 mg/ml, (FIG. 1B) 5 mg/ml. Images were taken at 2000× magnification, scale bar –10 um.

(FIG. 2A) Hydrogel with concentration of 5 mg/ml, (FIG. 2B) 20 mg/ml. Images were taken at 2000× magnification, scale bar –10 μm.

(FIG. 3A) Amnion hydrogel with concentration of 4 mg/ml, (FIG. 3B) 6 mg/ml, and (FIG. 3C) 8 mg/ml. Images were taken at 2000× magnification, scale bar –10 μm.

(FIG. 10B) Animals treated with decellularized AM-ECM also showed a decrease in both the quantity and severity of adhesion formation (FIG. 10C). The AM-ECM animal shown in FIG. 10C did not have any adhesive disease and the peritoneal buttons and cecum were covered in a fine layer of AM-ECM hydrogel.

DETAILED DESCRIPTION

Figure 1:
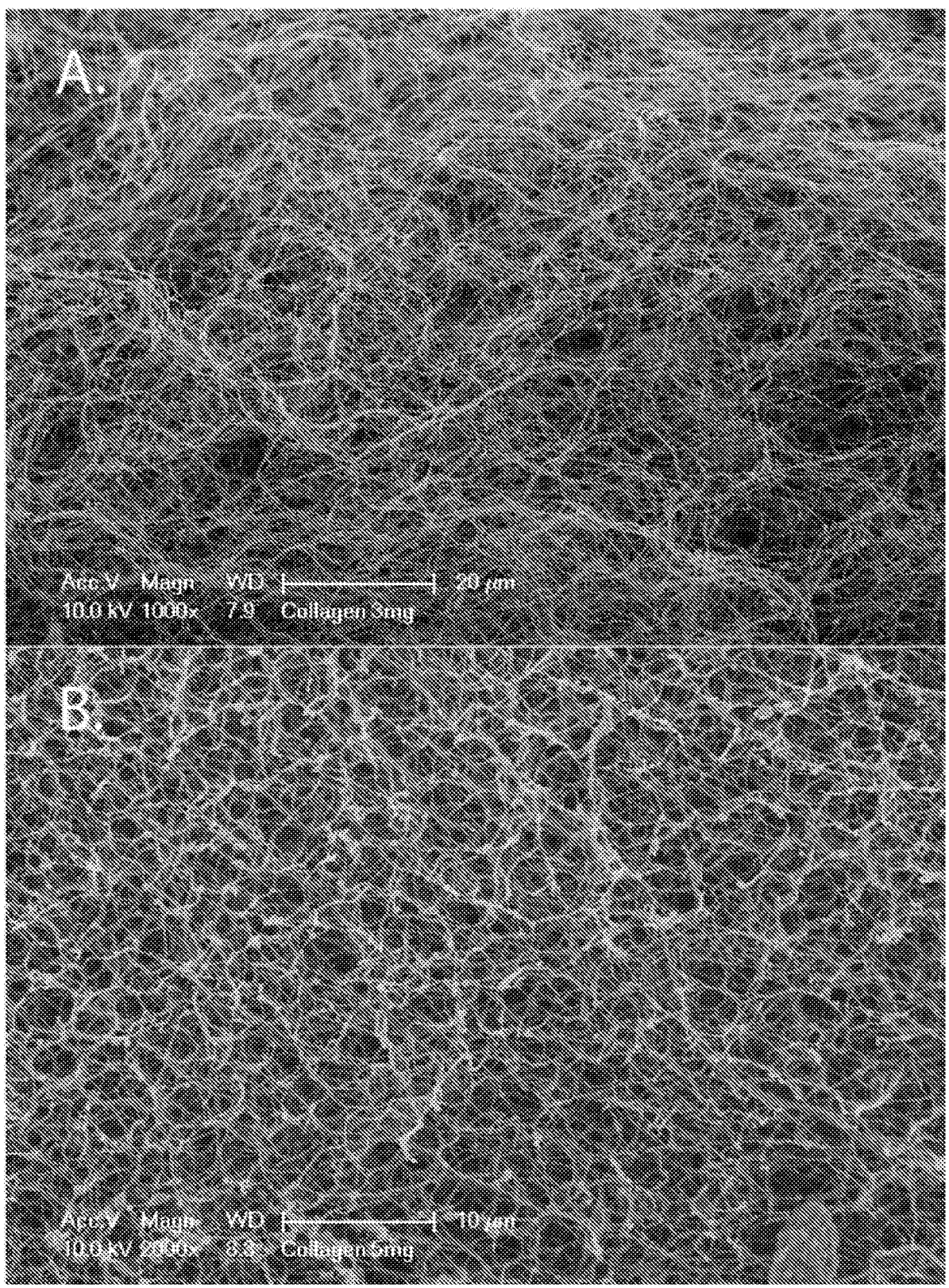
FIGS. 1A-1B show scanning electron microscopy images of collagen hydrogels.

The practice of the present technology will employ, unless otherwise indicated, conventional techniques of tissue culture, immunology, molecular biology, microbiology, cell biology, and recombinant DNA, which are within the skill of the art. See, e.g., Sambrook and Russell eds. (2001) *Molecular Cloning: A Laboratory Manual*, 3rd edition; the series Ausubel et al. eds. (2007) *Current Protocols in Molecular Biology*; the series *Methods in Enzymology* (Academic Press, Inc., N.Y.); MacPherson et al. (1991) *PCR 1: A Practical Approach* (IRL Press at Oxford University Press); MacPherson et al. (1995) *PCR 2: A Practical Approach*; Harlow and Lane eds. (1999) *Antibodies, A Laboratory Manual*; Freshney (2005) *Culture of Animal Cells: A Manual of Basic Technique*, 5th edition; Gait ed. (1984) *Oligonucleotide Synthesis*; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

As used herein, certain terms may have the following defined meanings. As used in the specification and claims, the singular form "a," "an" and "the" include singular and plural references unless the context clearly dictates otherwise. For example, the term "a cell" includes a single cell as well as a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

A "composition" is also intended to encompass a combination of active agent and another carrier, e.g., compound or composition, inert (for example, a detectable agent or label) or active, such as an adjuvant, diluent, binder, stabilizer, buffers, salts, lipophilic solvents, preservative, adjuvant or the like. Carriers also include pharmaceutical excipients and additives proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this invention, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The term "pharmaceutically acceptable carrier" (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. Pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

In one aspect, the term "hydrogel" intends hydrogel polymers of natural, recombinant or synthetic origin, or hybrids thereof, are introduced in a dry, less hydrated, or substantially deswollen state and rehydrate in a physiological environment to undergo a volumetric expansion and to affect sealing, plugging, or augmentation of tissue, defects in tissue, or of organs. The hydrogel polymers may deliver therapeutic entities by controlled release at the site. A non-limiting example of such is described in U.S. Pat. No. 7,780,980. As described by the '980 patent, hydrogels are materials that absorb solvents (such as water), undergo rapid swelling without discernible dissolution, and maintain three-dimensional networks capable of reversible deformation. See, e.g., Park, et al., *Biodegradable Hydrogels for Drug Delivery*, Technomic Pub. Co., Lancaster, Pa. (1993).

The hydrogels as used herein may be uncrosslinked or crosslinked. The hydrogels may be formed by physical or chemical crosslinking, or a combination of these two processes. As described in the '980 patent, physical crosslinking takes place as a result of ionic linkages, hydrogen bonding, Van der Waals forces, or other such physical forces. Chemical crosslinking occurs due to the formation of covalent linkages. Covalently crosslinked networks of hydrophilic polymers, including water-soluble polymers are traditionally denoted as hydrogels (or aquagels) in the hydrated state. Hydrogels have been prepared based on crosslinked polymeric chains of methoxypoly(ethylene glycol) monomethacrylate having variable lengths of the polyoxyethylene side chains, and their interaction with blood components has been studied (Nagaoka et al., in Polymers as Biomaterial (Shalaby et al., Eds.) Plenum Press, 1983, p. 381).

The term also includes matrices that are known to maintain and expand pluripotent and multipotent stem cells, for example Matrigel. Matrigel is the trade name for a gelatinous protein mixture secreted by Engelbreth-Holm-Swarm (EHS) mouse sarcoma cells produced and marketed by Corning Life Sciences. Trevigen, Inc. markets another version under the trade name Cultrex BME. Matrigel resembles the complex extracellular environment found in many tissues and is used as a substrate for culturing various types of pluripotent and multipotent stem cells. Additional examples include the PureCol® EZ Gel which is a Bovine Collagen Solution (Type I) for tissue engineering research, cell culture and Biochemistry (see advancedbiomatrix.com/collagen-type-i/purecol-ez-gel/).

Another example is Excellagen, which is a pharmaceutically formulated fibrillar Type I bovine collagen gel for wound care management. The flowable, ready to use formulation of Excellagen is ideal for use in wounds of varying shapes and surface contours as well as tunneled/undermined wounds where sheet-based products are not adequate. (See excellagen.com).

As used herein, the term "patient" or "subject" intends an animal, a mammal or yet further a human patient. For the purpose of illustration only, a mammal includes but is not limited to a human, a simian, a murine, a bovine, an equine, a porcine or an ovine.

The term "isolated" as used herein refers to molecules or biological or cellular materials being substantially free from other materials, e.g., greater than 70%, or 80%, or 85%, or 90%, or 95%, or 98%. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source and which allow the manipulation of the material to achieve results not achievable where present in its native or natural state, e.g., recombinant replication or manipulation by mutation. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides, e.g., with a purity greater than 70%, or 80%, or 85%, or 90%, or 95%, or 98%. The term "isolated" is also used herein to refer to cells or tissues that are isolated from other cells or tissues and is meant to encompass both cultured and engineered cells or tissues.

As used herein, "stem cell" defines a cell with the ability to divide for indefinite periods in culture and give rise to specialized cells. At this time and for convenience, stem cells are categorized as somatic (adult) or embryonic. A somatic stem cell is an undifferentiated cell found in a differentiated tissue that can renew itself (clonal) and (with certain limitations) differentiate to yield all the specialized cell types of the tissue from which it originated. An embryonic stem cell is a primitive (undifferentiated) cell from the embryo that has the potential to become a wide variety of specialized cell types. An embryonic stem cell is one that has been cultured under in vitro conditions that allow proliferation without differentiation for months to years. Pluripotent embryonic stem cells can be distinguished from other types of cells by the use of marker including, but not limited to, Oct-4, alkaline phosphatase, CD30, TDGF-1, GCTM-2, Genesis, Germ cell nuclear factor, SSEA1, SSEA3, and SSEA4. The term "stem cell" also includes "dedifferentiated" stem cells, an example of which is a somatic cell which is directly converted to a stem cell, i.e., reprogrammed. A clone is a line of cells that is genetically identical to the originating cell; in this case, a stem cell.

An "induced pluripotent cell" intends embryonic-like cells reprogrammed to the immature phenotype from adult cells. Various methods are known in the art, e.g., "A simple new way to induce pluripotency" Nature, 29 Jan. 2014 and available at sciencedaily.com/releases/2014/01/140129184445, last accessed on Feb. 5, 2014 and U.S. Patent Publication No. 2010/0041054. Human iPSCs also express stem cell markers and are capable of generating cells characteristic of all three germ layers.

The term "propagate" means to grow or alter the phenotype of a cell or population of cells. The term "growing" or "expanding" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue.

The term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

"Clonal proliferation" refers to the growth of a population of cells by the continuous division of single cells into two identical daughter cells and/or population of identical cells.

As used herein, the "lineage" of a cell defines the heredity of the cell, i.e. its predecessors and progeny. The lineage of a cell places the cell within a hereditary scheme of development and differentiation.

"Differentiation" describes the process whereby an unspecialized cell acquires the features of a specialized cell such as a heart, liver, or muscle cell. "Directed differentiation" refers to the manipulation of stem cell culture conditions to induce differentiation into a particular cell type or phenotype. "Dedifferentiated" defines a cell that reverts to a less committed position within the lineage of a cell. As used herein, the term "differentiates or differentiated" defines a cell that takes on a more committed ("differentiated") position within the lineage of a cell. As used herein, "a cell that differentiates into a mesodermal (or ectodermal or endodermal) lineage" defines a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, leiomyogenic, chondrogenic, cardiogenic, dermatogenic, hematopoetic, hemangiogenic, myogenic, nephrogenic, urogenitogenic, osteogenic, pericardiogenic, or stromal.

Examples of cells that differentiate into ectodermal lineage include, but are not limited to epidermal cells, neurogenic cells, and neurogliagenic cells.

Examples of cells that differentiate into endodermal lineage include, but are not limited to pleurogenic cells, and hepatogenic cells, cell that give rise to the lining of the intestine, and cells that give rise to pancreogenic and splanchogenic cells.

As used herein, a "pluripotent cell" defines a less differentiated cell that can give rise to at least two distinct (genotypically and/or phenotypically) further differentiated progeny cells.

A "multi-lineage stem cell" or "multipotent stem cell" refers to a stem cell that reproduces itself and at least two further differentiated progeny cells from distinct developmental lineages. The lineages can be from the same germ layer (i.e., mesoderm, ectoderm or endoderm), or from different germ layers. An example of two progeny cells with distinct developmental lineages from differentiation of a multilineage stem cell is a myogenic cell and an adipogenic cell (both are of mesodermal origin, yet give rise to different tissues). Another example is a neurogenic cell (of ectodermal origin) and adipogenic cell (of mesodermal origin).

As used herein, the term "treating" is meant administering a pharmaceutical composition for the purpose of improving the condition of a patient by reducing, alleviating, reversing, or preventing at least one adverse effect or symptom.

As used herein, the term "preventing" is meant identifying a subject (i.e., a patient) having an increased susceptibility to a disease but not yet exhibiting symptoms of the disease, and administering a therapy according to the principles of this disclosure. The preventive therapy is designed to reduce the likelihood that the susceptible subject will later become symptomatic or that the disease will be delay in onset or progress more slowly than it would in the absence of the preventive therapy. A subject may be identified as having an increased likelihood of developing the disease by any appropriate method including, for example, by identifying a family history of the disease or other degenerative brain disorder, or having one or more diagnostic markers indicative of disease or susceptibility to disease.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, inhalation, injection, and topical application.

MODES FOR CARRYING OUT THE DISCLOSURE

This disclosure provides an isolated decelluarized amniotic membrane (DCM). In one aspect, the isolated DCM is further processed, e.g., freezing, freeze drying, lyophilization and/or micronized into powder or treatment with pepsin to create a hydrogel.

In another aspect, the isolated DCM further comprises, or alternatively consists essentially of, or yet further consists of, a carrier such as a pharmaceutically acceptable carrier. Non-limiting examples pharmaceutically acceptable carriers include one or more of phosphate buffered saline, deionized water, a hydrogel or a collagen-based product. In one aspect, the isolated DCM is derived from placenta isolated from a human, a bovine, an equine, a feline, a canine or a murine.

In another aspect, the compositions or DCM further comprises, or alternatively consists essentially of, or yet further consists of, one or more of a therapeutic cell, such as a genetically engineered cell (e.g., prokaryotic or eukaryotic), e.g., a stem cell, such as a mesenchymal stem cell. The stem cell can be from any appropriate animal source, e.g., a human, a bovine, an equine, a feline, a canine or a murine. It can be autologous or allogeneic to the subject being treated.

Further provided is a method to culture a cell comprising, or alternatively consisting essentially of, or yet further consisting of, mixing the cell with the DCM hydrogel as described above, and culturing the cell under conditions that favor growth and expansion of the cell. The mixing can be in vitro or in vivo. The cell can be one or more of a therapeutic cell, such as a genetically engineered cell (e.g., prokaryotic or eukaryotic), e.g., a stem cell, such as a mesenchymal stem cell. The stem cell can be from any appropriate animal source, e.g., a human, a bovine, an equine, a feline, a canine or a murine. It can be autologous or allogeneic to the subject being treated.

Also provided is method to treat a wound, comprising, or alternatively consisting essentially of, or yet further consisting of, administering to a subject in need thereof, an effective amount of the isolated DCM and/or the compositions as described herein, thereby treating the wound. Additional therapies and/or compositions can be combined with the therapeutic application, e.g., antibiotics, growth factors, and the like. The co-administration can be concurrent or sequential as determined by the treating physician or veterinarian. Thus, the methods can be used in animals as well as humans and the source of DCM is selected for use in the subject.

Also provided is a method for treating or preventing inflammation in a subject in need thereof, comprising, or alternatively consisting essentially of, or yet further consisting of, administering to the subject an effective amount the isolated DCM and/or the compositions as described herein, thereby treating or preventing inflammation. Additional therapies and/or compositions can be combined with the therapeutic application, e.g., anti-inflammatories, e.g., steroids, and the like. The co-administration can be concurrent or sequential as determined by the treating physician or veterinarian. Thus, the methods can be used in animals as well as humans.

Yet further provided is a method for treating or preventing adhesion or scar formation in a subject in need thereof, comprising, or alternatively consisting essentially of, or yet further consisting of, an effective amount the isolated DCM and/or the compositions as described herein, thereby treating or preventing adhesion or scar formation. Additional therapies and/or compositions can be combined with the therapeutic application, e.g., anti-inflammatories, e.g., steroids, and the like. The co-administration can be concurrent or sequential as determined by the treating physician or veterinarian. Thus, the methods can be used in animals as well as humans.

In the disclosed methods, administration comprises one or more of topical, intraperitoneal, local, or systemic and in one aspect, the composition further comprises stem cells.

The cells or compositions can be autologous or allogeneic to the subject being treated and the subject is any suitable subject, non-limiting examples of such include a human, a bovine, an equine, a feline, a canine or a murine.

Further provided is a kit comprising, or alternatively consisting essentially of, or yet further consisting of, the isolated DCM and/or the composition as described herein, and optionally instruction to perform the methods and prepare the compositions and DCM as disclosed herein.

EXPERIMENTAL

Example 1

Amniotic Membrane Decellularization

Term placenta is obtained from the University of California, Davis Medical Center Obstetrics Department following either vaginal or cesarean delivery. The placenta is brought to the Surgical Bioengineering Lab and the amniotic membrane is dissected from the chorionic plate using blunt dissection. The amnion is washed in 1×PBS and then frozen in a −20° C. freezer until it needs to be utilized for decellularization.

At the time of decellularization, the amniotic membrane is removed from the freezer, thawed decellularized utilizing a protocol developed by Brown et al. that has subsequently been modified for amniotic membrane (Brown, B. et al. (2006) Tissue Engineering 12:519-526) (Table I).

TABLE I

| Amniotic Membrane Decellularization Protocol | |
|---|---|
|  | Time |
| Weighed amniotic membrane |  |
| Freeze and thaw amniotic membrane | 24 hour cycle × 3 |
| De-ionized water wash | 30 minutes × 3 |
| 0.02% trypsin/0.05% EDTA | 1 hour |
| De-ionized water rinse with massage |  |
| 3% Triton X-100 | 1 hour |
| De-ionized water rinse with massage |  |
| 4% sodium deoxycholic acid | 1 hour |
| De-ionized water rinse with massage |  |
| 0.1% peracetic acid/4% ethanol | 2 hours |
| 1X Phosphate buffered solution (PBS) rinse | 15 minutes |
| De-ionized water wash | 15 minutes × 2 |
| Remove excess deionized water and freeze product in the −20° C. freezer |  |

As is apparent to the skilled artisan, the above times and compositions can be varied and still be within the scope and spirit of this invention. For example, provided herein is a method to decellularize amniotic membrane tissue comprising, or alternatively consisting essentially of, or yet further consisting of: freezing and thawing amniotic membrane tissue isolated from a suitable host for at least two, or at least three, or at least four or more cycles, with each cycle being from between 20 to about 25 hours, or alternatively from between 22 to 27 hours, or alternatively from between 23 to 26 hours or alternatively about 24 hour cycles. The product is then massaged for 10 dun and washed with de-ionized water for about 30 minutes for at least 2, or alternatively at least 3, or alternatively at least 4 cycles. A detergent solution is added to lyse cells and aid in decellularization, such as 3% Triton X-100 (t-Octylphenoxypolyethoxyethanol), and the composition is transferred to shaker a for about one hour, and then rinsed with de-ionized water for about 1 hour, or at least 30 minutes to remove the detergent solution. A 4% sodium deoxycholic acid solution is added to the product to further decellularize the tissue and the composition is transferred to a Stoval Belly Dancer for at least 30 minutes, or at least an hour, followed by a de-ionized water massage as noted above. The product is returned to the shaker and a solution of about 0.1% peracetic acid/4% ethanol is added for at least 1.5 hours, or at least 2 hours, to disinfect and remove residual nucleic acids from the ECM with minimal effects to the composition and structure. The composition is then rinsed with 1×Phosphate buffered solution (PBS) on shaker for at least 10 minutes, or alternatively at least 15 minutes. The product is rinsed again (at least once, or twice or more) with de-ionized water wash on shaker for at least 10 minutes, or alternatively at least 15 minutes. Excess water is removed and the product can be frozen or further processed for storage.

Following decellularization, the amniotic membrane is frozen down for preservation. The decellularized membrane can then be used as described herein, e.g., for the creation of a decellularized amniotic membrane derived extracellular matrix hydrogel for stem cell delivery, cell culture and tissue engineering and/or prevention of abdominal adhesions using decellularized amnion sheets or decellularized amniotic membrane derived extracellular matrix hydrogel, as well as the treatment of disease or conditions where such issues are implicated.

Decellularized Human Amniotic Membrane Derived Extracellular Matrix (AM-ECM) Hydrogel—a Novel Scaffold for Stem Cell Delivery, Cell Culture and Tissue Engineering Stem cells have great potential for tissue engineering and other cell-based therapeutic applications. But current regenerative strategies utilizing stem cells are often limited by poor cellular survival, distribution and integration after transplantation in part due to the poor method of stem cell delivery to the site of tissue injury. This problem has been partially overcome through the use of hydrogels that support three-dimensional cell culture. However, to optimize the therapeutic potential of stem cells, a new cell delivery vehicle that maintains cell viability and facilitates integration needs to be created.

Appropriate matrices are needed to maintain and expand pluripotent and multipotent stem cells. One good example of matrices is Matrigel. Matrigel is the trade name for a gelatinous protein mixture secreted by Engelbreth-Holm-Swarm (EHS) mouse sarcoma cells produced and marketed by Corning Life Sciences. Trevigen, Inc. markets their own version under the trade name Cultrex BME. Matrigel resembles the complex extracellular environment found in many tissues and is used as a substrate for culturing various types of pluripotent and multipotent stem cells. However, its sarcoma source has made it impossible to be used for clinical applications. There are some other matrices that have been developed for stem cell expansion, delivery, or wound management. For example, the PureCol® EZ Gel which is a Bovine Collagen Solution (Type I) for tissue engineering research, cell culture and Biochemistry: (advancedbiomatrix.com/collagen-type-i/purecol-ez-gel).

Another example is Excellagen, which is a pharmaceutically formulated fibrillar Type I bovine collagen gel for wound care management. The flowable, ready to use formulation of Excellagen is ideal for use in wounds of varying shapes and surface contours as well as tunneled/undermined wounds where sheet-based products are not adequate (excellagen.com).

So far, no human-derived (xeno-free) hydrogel matrix for human stem cell culture, expansion and delivery is available on market.

To this end, extracellular matrix made from decellularized human amnion membrane (AM-ECM, in the formats of sheet and hydrogel) are provided for propagating and expanding human stem cells as well as for stem cell delivery. AM-ECM hydrogel is a promising material for use in tissue repair and regeneration due to its immuoregulatory and angiogenic nature, its biocompatibility, and the ability of AM-ECM to biodegrade through a natural process. Furthermore, following childbirth, the placenta is an accessible organ that should be utilized and can be stored for future use Methods Placenta Derived Mesenchymal Stem Cell Culture Multipotent mesenchymal stem cells derived from various sources, such as bone marrow or placenta, hold great promise for cell-based therapies. Several recent publications suggest that placenta derived mesenchymal stem cells (PMSCs) have a wide range of applications, and can serve as an effective alternative to bone marrow stromal cells (Lankford, L. et al. (2015) World Journal of Stem Cells 7:195-207; Parolini, O. et al. (2011) Placenta 32(Suppl 2):S186-5195). In this study, Applicants use human PMSCs as an example. PMSCs were isolated from placental tissue obtained from routine births and surgical cases at UC Davis Medical Center in Sacramento, Calif. Cells were expanded in 5% FBS DMEM supplemented with 20 ng/ml bFGF and 20 ng/ml EGF, in 37° C., 5% $CO_2$ incubator.

Preparation of Hydrogel

Following decellularization, the amniotic membrane is lyophilized (freeze dried) and stored in sterile containers at room temperature until hydrogel creation. Hydrogels are created using a modified protocol developed by Wolf et al. (Wolf, M. T. et al. (2012) Biomaterials 33:7028-7038) (Table II).

TABLE II

Decellularized AM-ECM Hydrogel Protocol

Determine weight of decellularized lyophilized product

Shred decellularized product in >3 mm fragments

Dilute decellularized product with milli-Q water until a concentration of 10 mg ECM/mL is achieved Add 1 mg/mL of porcine pepsin to the solution Add 1M hydrochloric acid (HCl) to the solution to achieve a 0.01N HCl solution Stir the solution a constant rate at room temperature × 72 hours TABLE II-continued Decellularized AM-ECM Hydrogel Protocol The solution can be frozen in −20° C. for later use or used for gelation immediately
To induce gelation, neutralize the pH of the solution by adding 1/10th the volume of 0.1N NaOH
Add 1/9th the digest volume of 10X PBS As is apparent to the skilled artisan, the above times and compositions can be varied and still be within the scope and spirit of this invention. Thus, this disclosure provides a method to decellularize AM-ECM to provide a hydrogel matrix. The decelluarized product is shredded to about 3 mm fragments and mixed with milli-Q water or an equivalent thereof to reach a concentration of about 8 to 15, or alternatively from about 11 to 13, or alternatively of about 10 mg ECM/mL is achieved. An effective amount of pepsin is added at a concentration of about 1 mg/mL. About 1 M HCl or other equivalent acid is added to achieve a 0.01 n HCl solution and the resultant solution if mixed, e.g, by stirring, at room temperature for about 65 hours or more, or alternatively about 70 hours or more, or about 72 hours. The resultant solution can be frozen for storage or processed, e.g., by the addition of a stability agent, such as glycerol. Following neutralization, the AM-ECM is incubated at 37° C. for one hour to induce gelation.

Hydrogel Gelation Time Testing

Gelation dynamics data helped establish a protocol for injection of the cells embedded in hydrogel. Gelation time of fibrin glue was determined by quantifying changes in turbidity upon the combination of solutions with various concentrations of fibrinogen and thrombin. Collagen and amnion hydrogels were prepared on ice. For each group 100 ml/well of gel was added in 96-well plate in triplicates. The turbidity of material then was measured spectrophotometrically with a microplate reader at 55 0 nm every minute for 60 minutes at 37° C. in triplicates.

Evaluation of Hydrogel Nanostructure

Scanning Electron Microscopy was utilized to evaluate scaffold morphology. Hydrogel molds were prepared by pouring 500 ul of gel per well in wells of 48-well plate and allowed to polymerize at 37° C. for 1 hour. Next they were fixed overnight with 2.5% concentration of glutaraldehyde in cacodylate buffer at 4° C. Next gels were washed in series of ethanol concentrations in distilled water for dehydration: 40%, 60%, 75%, 85%, 90%, 95%, and 100%. After critical pointdrying, gels were coated with metal 3 times using a sputter coater (Pelco Auto Sputter Coater SC-7) and imaged with a scanning electron microscope (Phillips XL30 TMP).

In Vitro MSC Viability and Proliferation Tests

Placenta derived Mesenchymal Stem cells (PMSCs) were incorporated in hydrogels at final concentration of $1\times10^4$ cells/200 ul/well of 96-well non TC-treated plate. Following gelation, cell-seeded hydrogel constructs were placed in 37° C. $CO_2$ incubator for 1 day, 4 days and 6 days periods. CellTiter 96 AQueous One Solution Cell Proliferation Assay was used to assess the relative number of proliferating cells. Cell proliferation measurements were performed in triplicates.

Biochemical Composition of Hydrogel

In order to analyze the components of AM-ECM, a series of biochemical analyses are being performed. AM-ECM derived hydrogel was neutralized and assayed for collagen, elastin and GAG protein concentration. The concentration of acid-pepsin soluble collagens (Types I to V) was determined using Sircol soluble collagen assay kit (Biocolor). Elastin was quantified using Fastin Elastin Assay kit (Biocolor). Sulfated proteoglycans and glycosaminoglycans measured using the Blyscan assay kit (Biocolor). These studies are still in progress.

Cytokine Array Analysis of PMSC Secreted Proteins

Angiogenesis related secreted factors were analyzed from the culture supernatant. PMSCs were seeded at a density of $1\times10^5$ per 1 ml of hydrogel per well of 6-well plate. Culture supernatants were collected at 24 h, centrifuged to remove particulates and then assessed for the relative levels of 55 angiogenesis-related cytokines using Proteome Profiler™ Human Angiogenesis Antibody Array kit according to the manufacturer's instructions (R&D Systems). Supernatants from a monolayer cell culture as well as from amnion gel and growth media were also collected as negative controls. Stained membrane blots were imaged on a Bio-Rad Chemi-Doc MP, and images were analyzed using ImageJ software with the Dot Blot Analysis plugin. Integrated density values obtained from membrane images were then plotted using Microsoft Excel.

Amnion Hydrogel Compatibility

Applicants also tested amnion hydrogel compatibility with other cells lines, including C2C12 myoblasts, bone marrow derived MSCs and SH-SY5Y neuroblastoma cells. Briefly, cells were mixed with decellularized amnion digests to form cell-seeded hydrogel constructs with density of $1\times10^5$ cells per 1 ml of hydrogel (6 mg/ml) per well of 6-well plate and placed in 37° C. $CO_2$ incubator for 1 hour to gel at 37° C. for 1 h to gel before the addition of 2 mL culture media to cover the hydrogel. Cell-seeded hydrogel constructs were incubated for 3 days. Cell viability was performed using commercially available LIVE/DEAD® Viability/Cytotoxicity assay (LifeTechnologies). Stained constructs were imaged using a Carl Zeiss Axio Observer D1 inverted microscope, and images were processed with ImageJ software.

Gelation Kinetics

Figure 4:
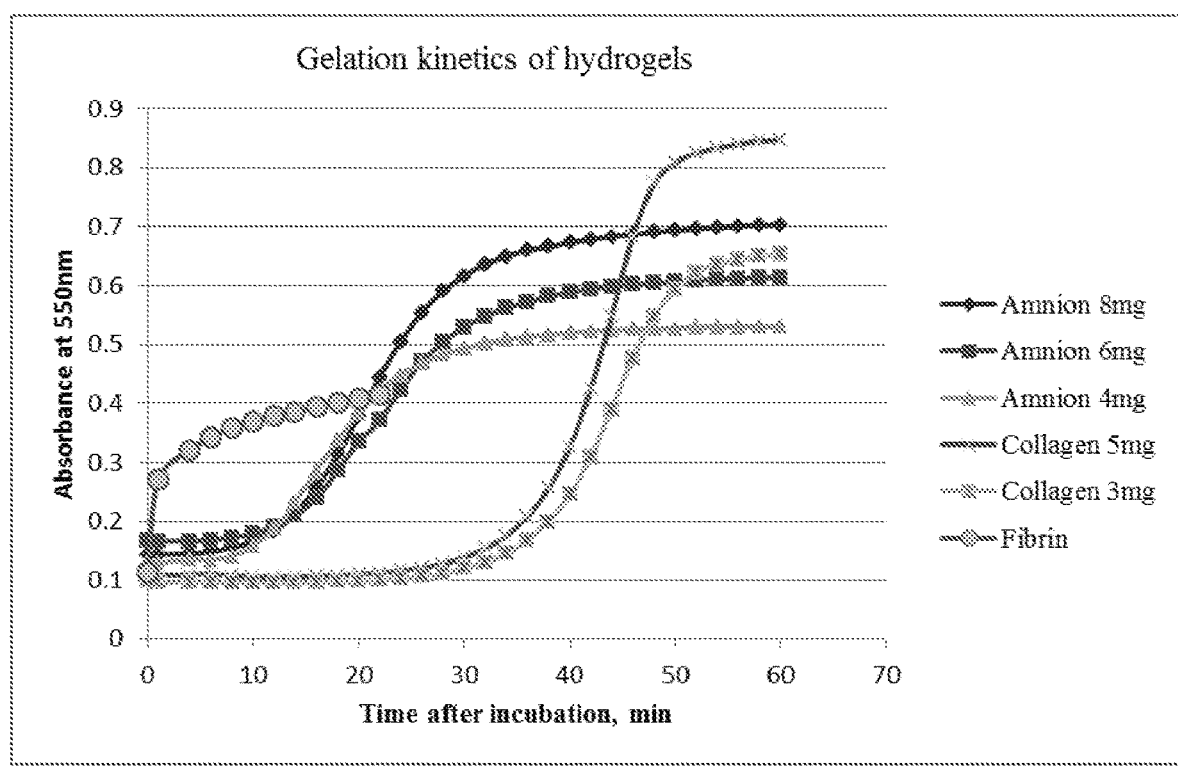
FIG. 4 shows gelation kinetics of hydrogels. Measured spectrophotometrically at 500 nm.

Fibrin gel becomes solid quickly within 1-2 minutes even with very low thrombin (10 U/ml) concentration (FIG. 4). This makes it useful when quick polymerization is required, e.g., cell delivery into the fluid abundant compartments. Amnion hydrogel reached 90% of its rigidity within 30 minutes after incubation initiation. While increased concentration plays a role in physical gel density, it did not affect its gelation time. When compared to collagen hydrogel, amnion derived hydrogel polymerizes at least 15 minutes earlier. This phenomenon can be attributed to the presence of cross-linking proteins in complex amnion scaffold.

Figure 5:
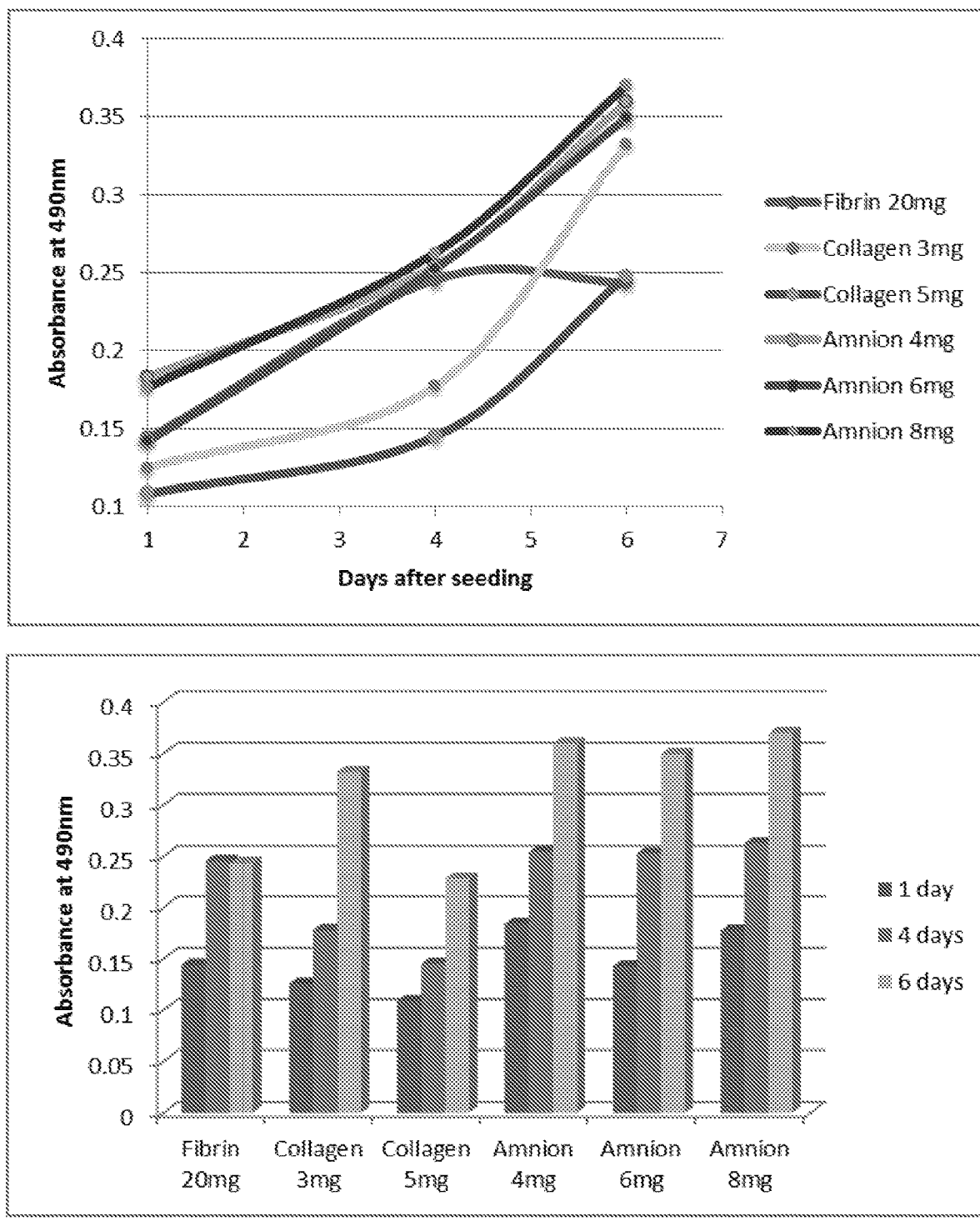
FIG. 5 shows proliferation of PMSCs in various hydrogels. Fibrin hydrogel with concentration of 20 mg/ml, collagen hydrogels with concentration of 3 and 5 mg/ml and amnion hydrogels with concentration of 6 and 8 mg/ml.

PMSCs proliferate in amnion hydrogel as good as or better than in collagen hydrogel (FIG. 5). Hydrogels with lower concentration seem to better support cellular proliferation. At day 4 Applicants noticed the degradation of fibrin 5 mg/ml matrix, and by day 6 most of it was degraded, making it impossible to assess corresponding cellular propagation. Fibrin gel at 20 mg/ml concentration retained most of its volume, but significant portion of it was degraded by day 6.

Figure 6:
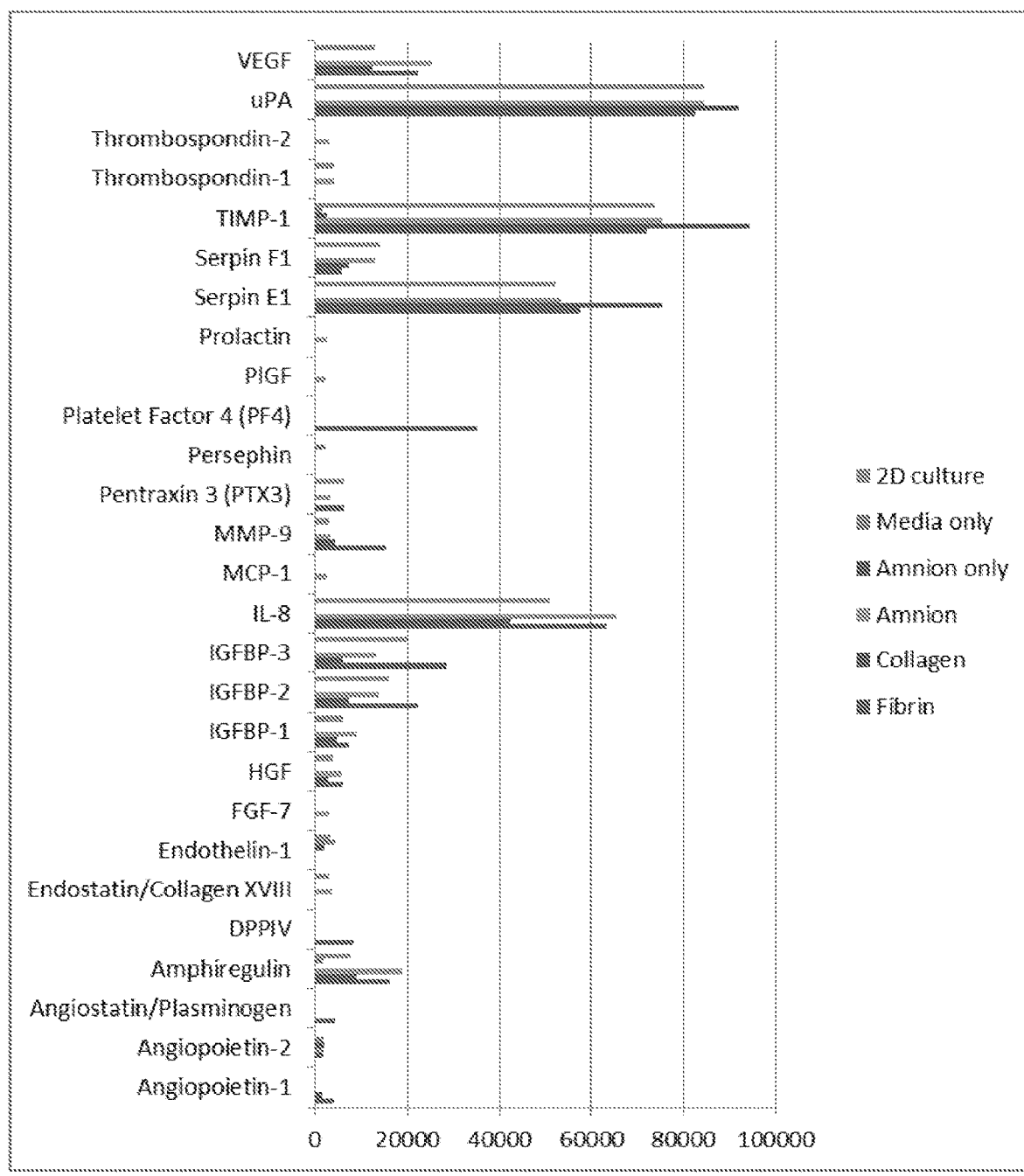
FIG. 6 shows paracrine secretion of PMSCs embedded in amnion, collagen and fibrin hydrogels when compared to two-dimensional cell culture and controls. Factors with integrated density values above 103 are shown.
Figure 7:
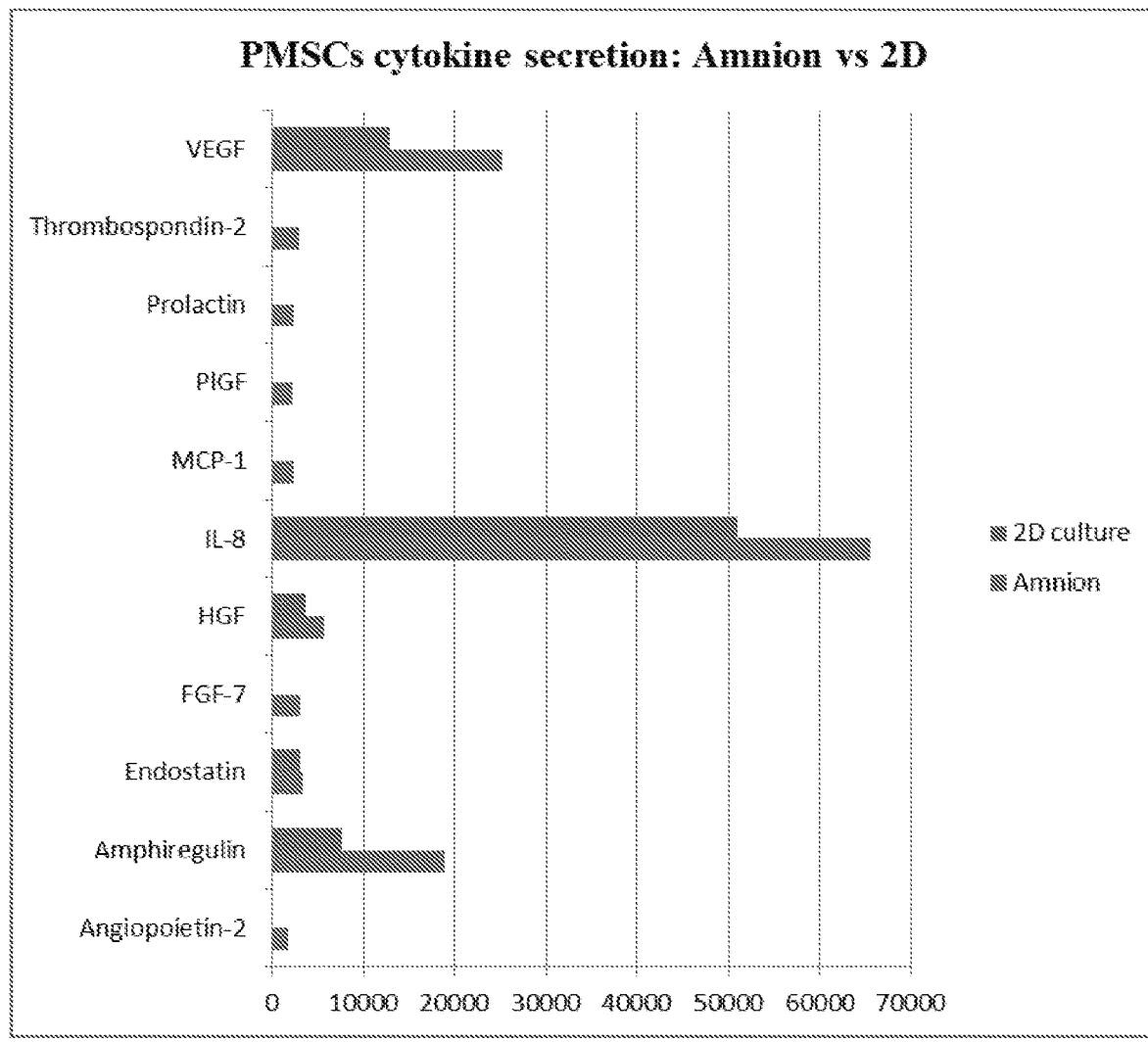
FIG. 7 shows paracrine secretion of PMSCs embedded in amnion hydrogel when compared to two-dimensional cell culture. Factors with integrated density values above $10^3$ are shown.
Figure 8:
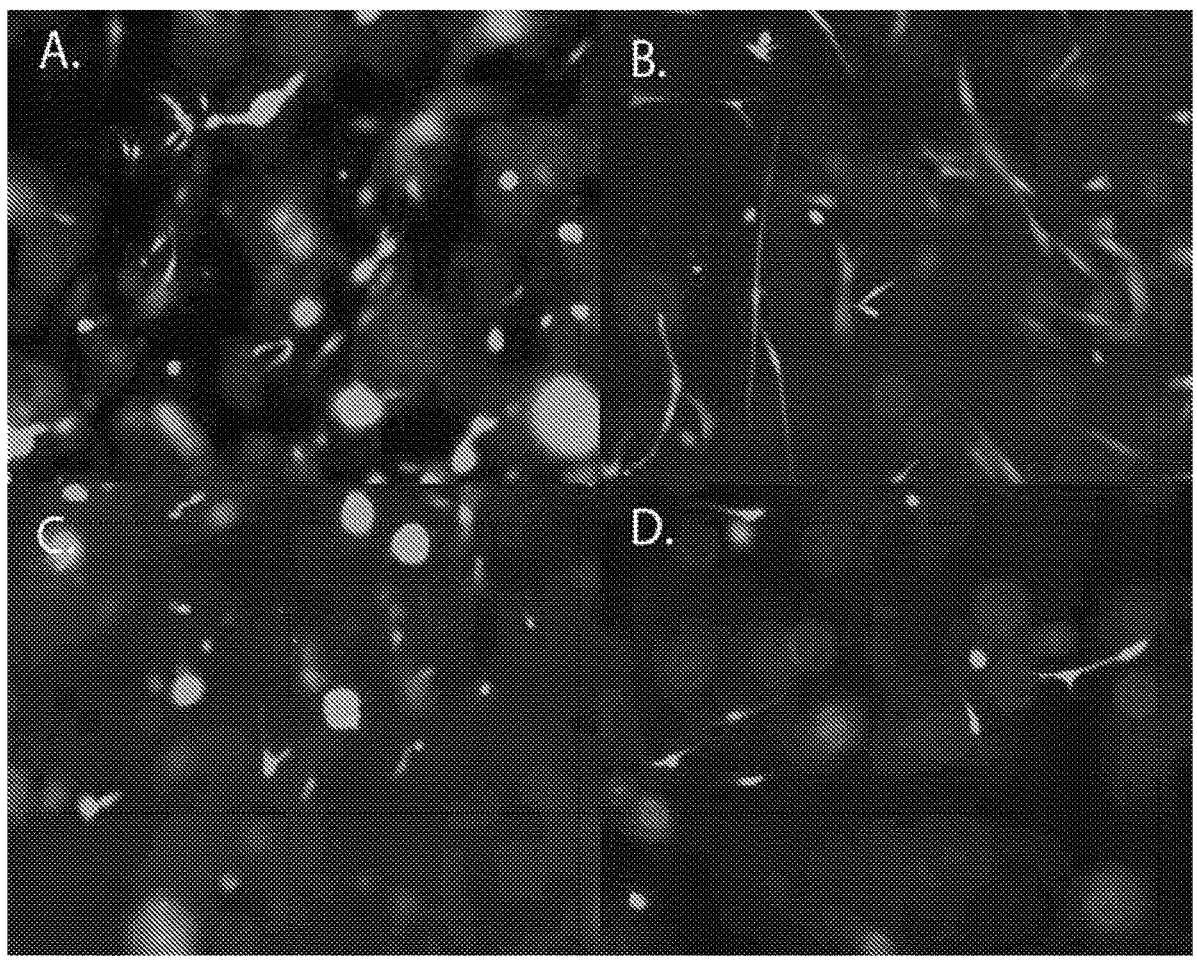
FIGS. 8A-8D shows live-dead fluorescent assay of stem cell hydrogel constructs. Amnion hydrogel with (FIG. 8A) C2C12 myoblasts, (FIG. 8B) PMSCs, (FIG. 8C) SH-SY5Y neuroblastoma cells, and (FIG. 8D). Bone marrow MSCs. Images were taken at 100× magnification.

According to results from the human angiogenesis array kit Applicants detected 27 factors secreted by PMSCs in hydrogels (FIG. 6). Generally, PMSCs shared their cytokine secretion profiles when cultured in hydrogels. Compared to a monolayer culture, some factors were upregulated in cells grown in 3D matrix supported culture, including vascular endothelial growth factor (VEGF), hepatocyte growth factor, thrombospndin-2, platelet factor 4, matrix metallopeptidase 9, and angiopoeitin. Fibrin based matrix stimulated secretion of platelet factor 4, matrix metallopeptidase 9, insulin-like growth factor-binding proteins 2 and 3, dipeptidyl peptidase 4 and angiostatin. PMSCs cultured in amnion hydrogel expressed elevated levels of placental growth factor (PlGF), VEGF, prolactin, IL-8, FGF-7 and amphiregulin (FIG. 7).

Amnion Hydrogel Compatibility

Results from the live-dead assay show that amnion derived hydrogel supports viability and expansion of various stem cell types, including C2C12 myoblasts, SH-SY5Y neuroblastoma cells, bone marrow and PMSCs. One can observe little red fluorescence, demonstrating that vast majority of cells is alive with intact membranes. All cell types exhibited their normal morphology, indicating that cells were well adhered in 3D matrix.

This data shows that AM-ECM hydrogel is an optimal cell delivery vehicle for PMSCs as well as other stem cells. Furthermore, AM-ECM is an easily obtainable and affordable human derived hydrogel that supports cellular attachment, proliferation and secretion, making it a promising candidate for regenerative medicine applications, such as tissue and organ engineering, wound healing, and tissue repair. Thus, this disclosure provides these therapeutic interventions comprising the use of the matrix described herein. The gelation dynamics are similar to that of collagen hydrogels making it a familiar alternative. AM-ECM also fills a void in the research and clinical market for a biocompatible human-derived (xeno-free) ECM matrix that supports 2D and 3D stem cell culture.

Discussion

Biological hydrogels that mimic extracellular matrix are novel candidates that support 3D cell culture and may be utilized for research as well as clinical applications such as tissue engineering and stem cell therapy. Amnion membrane decellularized extracellular matrix can be solubilized via pepsin digestion and form a hydrogel with similar biophysical characteristics as collagen and fibrin. On the nanoscale base, hydrogels produced with collagen at 3 mg/ml, fibrin at 5 mg/ml and amnion at 4 mg/ml concentrations exhibited similar fiber thickness and density as well as pore size. Fibrin clot polymerization is the fastest among hydrogels, and takes about 2-3 minutes. Amnion hydrogel solidifies within 25 minutes, whereas collagen based gel in about 45 minutes. Faster polymerization is desired in in vivo applications to limit hydrogel embedded stem cell loss from the site of application. Gel polymerization rate and mechanical strength can be further manipulated with non-cytotoxic cross-linking agents, such as transglutaminase and ribose via nonenzymatic glycation, and should be further investigated in stem cell therapy applications (Orban, J. M. et al. (2004) Journal of Biomedical Materials Research Part A. 68:756-762; Roy, R. et al. (2010) Journal of Biomedical Materials Research Part A. 93:843-851).

In vitro cell proliferation tests revealed the ability amnion hydrogel to support the growth of PMSCs. Moreover, cells embedded in amnion gel propagated at significantly higher rates when compared to collagen and fibrin embedded cells. Fibrin hydrogel degraded quickly due to cell secreted cytokines, and is unsuitable for 3D cell cultures lasting longer than 5 days. Protease inhibitors prolong the integrity of fibrin, but may limit its in vivo application due to undesirable side-effects. Interestingly, PMSCs consistently proliferated faster in hydrogels with lower fiber density. This can be explained by increased pore matrix sizes, aiding cellular motility and improved infiltration of the hydrogel molds.

Scientists agree that many of the therapeutic properties of mesenchymal stem cells are derivative of their paracrine activity (Murphy, M. B. et al. (2013) Experimental & Molecular Medicine 45:e54). Cytokine secretion assay demonstrated that, despite generally similar secretion profiles among hydrogel embedded PMSCs, extracellular scaffold derived variations in secretion levels of specific cytokines exist. Most notably, stem cells altered their secretion configurations when they were cultured in fibrin and amnion gels. Fibrin is utilized in the beginning of the wound healing cascade upon the clotting factors release by platelets (Diegelmann, R. F. et al. (2004) Front Biosci. 9:283-289). Fibrin clot plays an essential role in hemostasis, wound structural support, cell adhesion and migration (Midwood, K. S. et al. (2004) The International Journal of Biochemistry & Cell Biology 36:1031-1037). Predictably, MSCs cultured in fibrin express elevated levels of cytokines involved in wound healing. Platelet factor 4, also known as chemokine (C-X-C motif) ligand 4, binds to heparin, promoting blood coagulation, and is involved in angiogenesis and inflammation (Gupta, S. K. et al. (1995) Proc Nat Acad Sci USA. 92:7799-7803). Matrix metallopeptidase 9 (type IV collagenase) participates in degradation of extracellular matrix and cell migration (van Hinsbergh, V. W. et al. (2008) Cardiovascular Research 78:203-212). Insulin-like growth factor-binding proteins (IGFBP) regulate insulin-like growth factor activity, modulating cell cycle and apoptosis (Firth, S. M. et al. (2002) Endocrine Reviews 23:824-854). PMSCs that were cultured in amnion derived hydrogel were noted for expression of cytokines related to angiogenesis, such as placental growth factor and prolactin. PlGF along with VEGF play significant role in angiogenesis, endothelial cell migration and proliferation (Luttun, A. et al. (2002) Annals of the New York Academy of Sciences 979:80-93; Hoeben, A. et al. (2004) Pharmacological Reviews 56:549-580). Also amnion embedded MSCs secreted higher levels of IL-8 and FGF-7. IL-8 is known for chemotaxis of granulocytes, cell survival and proliferation (Li, A. et al. (2003) Journal of Immunology 170:3369-3376). FGF-7, aka keratinocyte growth factor, is a mitogen, and participates in neuroprotection and wound repair (Beer, H. D. et al. (2000) The Journal of Investigative Dermatology Symposium Proceedings 5:34-39). This data suggests that PMSCs can affect angiogenesis related processes in response the environmental signaling, and proper considerations should be taken when selecting cell delivery vehicle. To ensure the safety and effectiveness of stem cell therapy, cytokine secretion profiles should be carefully evaluated upon the delivery of MSCs to the target site.

Applicants' results supported the amnion derived hydrogel as novel candidate for delivery of PMSCs. This matrix maintained cellular attachment, proliferation, and physiology. Unlike collagen, it is human derived product, eliminating host rejection concerns. Amnion hydrogel supersedes fibrin in manufacturing cost, since it is produced from a readily available human tissue. Moreover, fibrin matrix is not suited for a prolonged cell culture due to its active digestion by cell-secreted cytokines.

To further investigate amnion hydrogel cell delivery capabilities, Applicants tested its compatibility with several widely-used cell lines. C2C12 are used to study myoblast differentiation, and are capable in producing skeletal muscle-like tissues (Donnelly, K. et al. (2010) Tissue Engineering Part C, Methods 16:711-718). SH-SYSY line serves as a model of neuronal function and differentiation, whereas bone marrow derived mesenchymal stem cells are current gold standard in MSC related therapies. All of these cells successfully adhered to the amnion hydrogel matrix, exhibited their usual morphology and proliferated at their normal rates. The number of dead cell detected in the live-dead assay was low if any.

Decellularized Amniotic Membrane and AM-ECM Hydrogel for the Prevention of Intra-Abdominal Adhesions Post-operative abdominal adhesions are a significant problem following abdominal and pelvic operations and have been noted to occur in up to 95% of patients who undergo re-operative abdominal or pelvic surgeries. Adhesions form secondary to the body's normal inflammatory response following injury to the peritoneal lining and viscera during surgical intervention. While this is a normal response, the result can cause significant morbidity including postoperative small bowel obstructions, chronic abdominal pain and female infertility (Barmparas, G. et al. (2010) Journal of Gastrointestinal Surgery: Official Journal of the Society for Surgery of the Alimentary Tract 14:1619-1628; Practice Committee of the American Society for Reproductive Medicine in collaboration with the Society of Reproductive Surgeons (2013) Fertility and Sterility 99:1550-1555; van Goor, H. (2007) Colorectal Disease: The Official Journal of the Association of Coloproctology of Great Britain and Ireland 9(Suppl 2):25-34). In addition, the presence of abdominal adhesions makes re-operation on the pelvis much more difficult and dangerous for the patient. These complications lead to a greater surgical workload and increased hospital resource utilization which translates to a significant economic burden with estimated annual costs of managing adhesive related problems exceeding $2 billion dollars in the United States alone (Sikirica, V. et al. (2011) BMC Surgery 11:13).

Intestinal obstruction secondary to adhesive disease is the most common cause of small bowel obstruction in the United States. One large review looking at over 20,000 hospital readmissions found that 5.7% of readmissions (over 1200 patients) were secondary to abdominal adhesions and 3.8% of these patients required re-operation (Ellis, H. et al. (1999) Lancet 353:1476-1480). With each subsequent procedure to manage adhesions, the incidence of having a postoperative bowel obstruction increases. The large number of readmissions and reoperations not only leads to increase risk of patient complications but also increases the cost of care and significantly affects a patient's quality of life.

Dense adhesions can also result in limited organ mobility, which leads to visceral pain resulting in chronic abdominal and/or pelvic pain (Diamond, M. P. et al. (2001) Human Reproduction Update 7:567-576). This again can lead to further operative intervention to try and alleviate the adhesive burden but more likely results in a significant amount of patient morbidity affecting quality of life.

Pelvic adhesions can prevent normal transport of the oocyte, which can result in infertility. This complication accounts for approximately 10% of all cases of female infertility (Practice Committee of the American Society for Reproductive Medicine in collaboration with the Society of Reproductive Surgeons (2013) Fertility and Sterility 99:1550-1555).

From an operative standpoint, 3 percent of all laparotomies are directly related to adhesions (Ellis, H. (1997) The European Journal of Surgery, Acta chirurgica Suppl.:5-9). These adhesions can complicate reoperation distorting tissue planes and anatomy but more importantly making abdominal re-entry more dangerous with a higher likelihood of inadvertent injury to the small bowel, bladder or ureters as well as an increased risk for blood loss.

Several medical device companies have looked at developing anti-adhesion products with limited success. The use of decellularized amniotic membrane and decellularized AM-ECM hydrogel could provide a breakthrough in the surgical field not only preventing procedural complication but also improving the quality of life in patients who have undergone abdominal and/or pelvic operations.

Amniotic membrane is a unique membrane that has been found to secrete several biologically active cytokines and growth factors, which are then stored in the thick basement membrane of the amnion are secreted over time. These biologic factors confer several natural therapeutic actions that would be beneficial in patients with abdominal adhesions including: (1) promotion of Epithelialization: The amniotic membrane has been found to secrete epidermal growth factor (EGF), keratinocyte growth factor (KGF), keratinocyte growth factor receptor (KGFR), hepatocyte growth factor (HGF), and hepatocyte growth factor receptor (HGFR), which are all known to promote healing and epithelialization. This would aid in peritoneal and visceral healing after injury during abdominal and pelvic operation preventing the formation of adhesions at the site of injury (Koizumi, N. J. et al. (2000) Current Eye Research 20:173-177);

(2) inhibition of Fibrosis: Amniotic membrane contains mesenchymal hyaluronic acid, which is known to inhibit transforming growth factor $\beta$ (TGF-$\beta$) a known pro-fibrotic growth factor. Preventing fibrosis could limit the number of adhesions formed (Sporn, M. B. et al. (1987) The Journal of Cell Biology 105:1039-1045);

(3) anti-inflammatory Properties: Metalloproteinase and interleukin-1 (IL-1) are known inflammatory mediators. Amniotic membrane secretes IL-1 receptor and metalloproteinase inhibitors, which can decrease the inflammatory cascade mediated by injured peritoneal and visceral surfaces during the post-operative period ultimately decreasing the likelihood of adhesions formation (Hao, Y. et al. (2000) Cornea 19:348-352).

The ability of the amniotic membrane to prevent fibrosis and inflammation, as well as aid in epithelialization, would be beneficial in preventing adhesion formation and in the healing of damaged native tissues. These characteristics have already lead to the use of amniotic membrane in the field of ophthalmology to protect and repair the cornea after corneal injury, chemical burns, corneal defects, ocular surgery and in patients with keratitis (Rahman, I. et al. (2009) Eye (London, England) 23:1954-1961; Sippel, K. C. et al. (2001) Current Opinion in Ophthalmology 12:269-281; Malhotra, C. et al. (2014) World Journal of Transplantation 4:111-121).

While amniotic membrane has been used successfully for ophthalmologic applications, the epithelial cell layer of the amniotic membrane could elicit an immune response causing an inflammatory reaction against the membrane leading to adhesion formation. Decellularized amniotic membrane would eliminate the immune reaction that could be mounted to the cellular component, improving immune tolerance towards the membrane making it a more effective anti-adhesion treatment.

Given the known characteristics of the amniotic membrane and combining it with a successful decellularized protocol would in theory provide a superior product for adhesion prevention and this has formed the rationale for the use of decellularized amniotic membrane and AM-ECM hydrogel.

In Vivo Methods

Utilizing the decellularized amniotic membrane and decellularized AM-ECM hydrogel to prevent postoperative abdominal adhesions is being conducted in a rodent model of abdominal adhesions. Several research groups have used this standardized model to investigate different therapies to prevent abdominal adhesions. The model consists of surgically inducing reproducible adhesions by creating ischemic peritoneal buttons in the left paracolic gutter and by mechanically abrading the cecum (Whang, S. H. et al. (2011) The Journal of Surgical Research 167:245-250).

Figure 9:
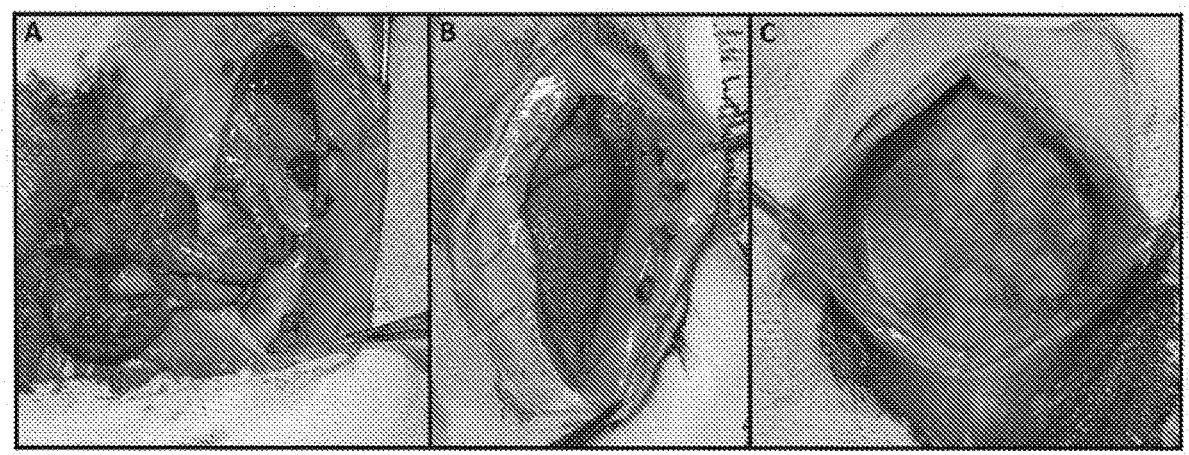
FIGS. 9A-9C show four peritoneal buttons are created in a standard location along the left paracolic gutter and the cecum is manually abraded to induce postoperative adhesions (FIG. 9A). Amniotic membrane (FIG. 9B) or 10 mL of AM-ECM hydrogel (FIG. 9C) is then placed in the abdominal cavity during the index procedure.

Applicants' procedures are performed on ~180-250 gram, female Sprague Dawley rats. After induction of general anesthesia, a four-centimeter midline incision is created. The abdomen is inspected for the presence of any pre-existing adhesions. If the abdomen is without adhesions, the adhesion creation procedure is performed. Four ischemic peritoneal buttons are created in the left paracolic gutter using 3-0 prolene suture. The cecum is also abraded circumferentially until punctate hemorrhage is induced. At the same operation, Applicants' decellularized products are applied. (FIG. 9) The abdominal wall of the rat is then closed and the rat is recovered from anesthesia. Routine postoperative care including daily weights, incision inspections and well-being checks are performed per protocol.

Two weeks following adhesion creation and treatment, rats are placed back general anesthesia and undergo exploratory laparotomy via a right paramedian trapdoor incision. The quantity and quality of adhesions are measured via standardized grading scales. (Whang, S. H. et al. (2011) The Journal of Surgical Research 167:245-250; Lucas, P. A. et al. (1996) The Journal of Surgical Research 65:135-138) (Table III). For the quantity of adhesions, the presence or absence of adhesions at each button is evaluated. For the quality of the adhesions, the density and vascularity of the adhesions are graded and given an overall score. These two scores are then added to develop a composite score of overall adhesion burden for each animal.

TABLE III

Adhesion Grading Scales

| Score | Adhesion Quantity | Adhesion Quality |
|---|---|---|
| 0 | No Adhesions | No adhesions |
| 1 | 25% buttons with adhesions | Filmy, avascular |
| 2 | 50% buttons with adhesions | Moderate, limited vascularity |
| 3 | 75% buttons with adhesions | Dense, well vascularized |
| 4 | 100% buttons with adhesions | |

Figure 10:
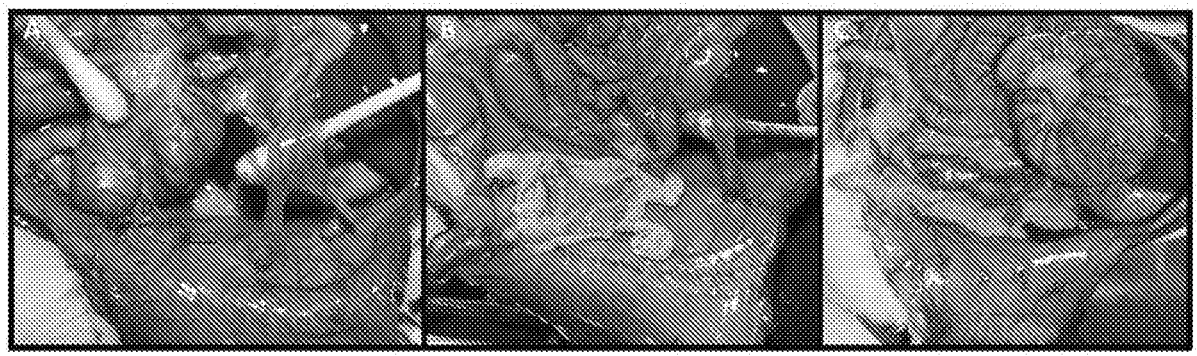
FIGS. 10A-10C show that the control animals show robust adhesion formation with adhesions at all four peritoneal buttons and moderate to dense adhesions (FIG. 10A). Animals treated with decellularized amniotic membrane demonstrate that the membrane prevents adhesion formation at the peritoneal buttons that are covered by the membrane.

Two control rats without any adhesion prevent treatment, two rats treated with decellularized amniotic membrane sheet, and two rats treated decellularized AM-ECM hydrogel have been completed. Both the use of amniotic membrane and AM-ECM hydrogel, as a treatment to prevent adhesions, appears to not only decrease the quantity but also the quality of adhesions at in this study. (FIG. 10, Table IV) Histologic analysis is pending.

TABLE IV

Pilot Rodent Adhesion Studies

| Study # | Treatment | Adhesion Quantity | Adhesion Quality |
|---|---|---|---|
| Rat 001 | None | 4 | 3 |
| Rat 002 | None | 4 | 4 |
| Rat 003 | Decell AM | 2 | 2 |
| Rat 004 | Decell AM | 1 | 3 |
| Rat 005 | AM-ECM Hydrogel | 3 | 2 |
| Rat 006 | AM-ECM Hydrogel | 0 | 0 |

Figure 2:
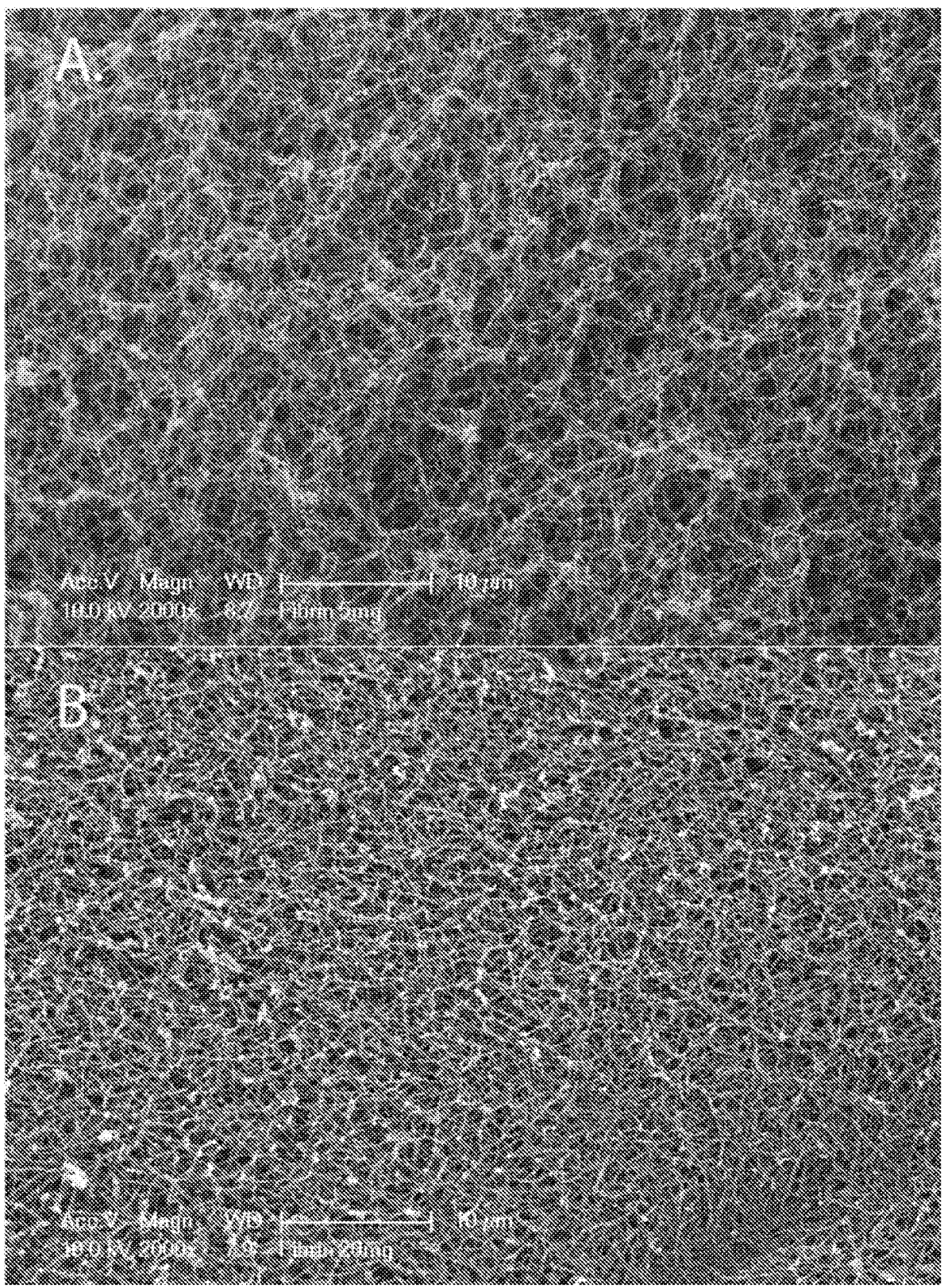
FIGS. 2A-2B show scanning electron microscopy images of fibrin hydrogels.
Figure 3:
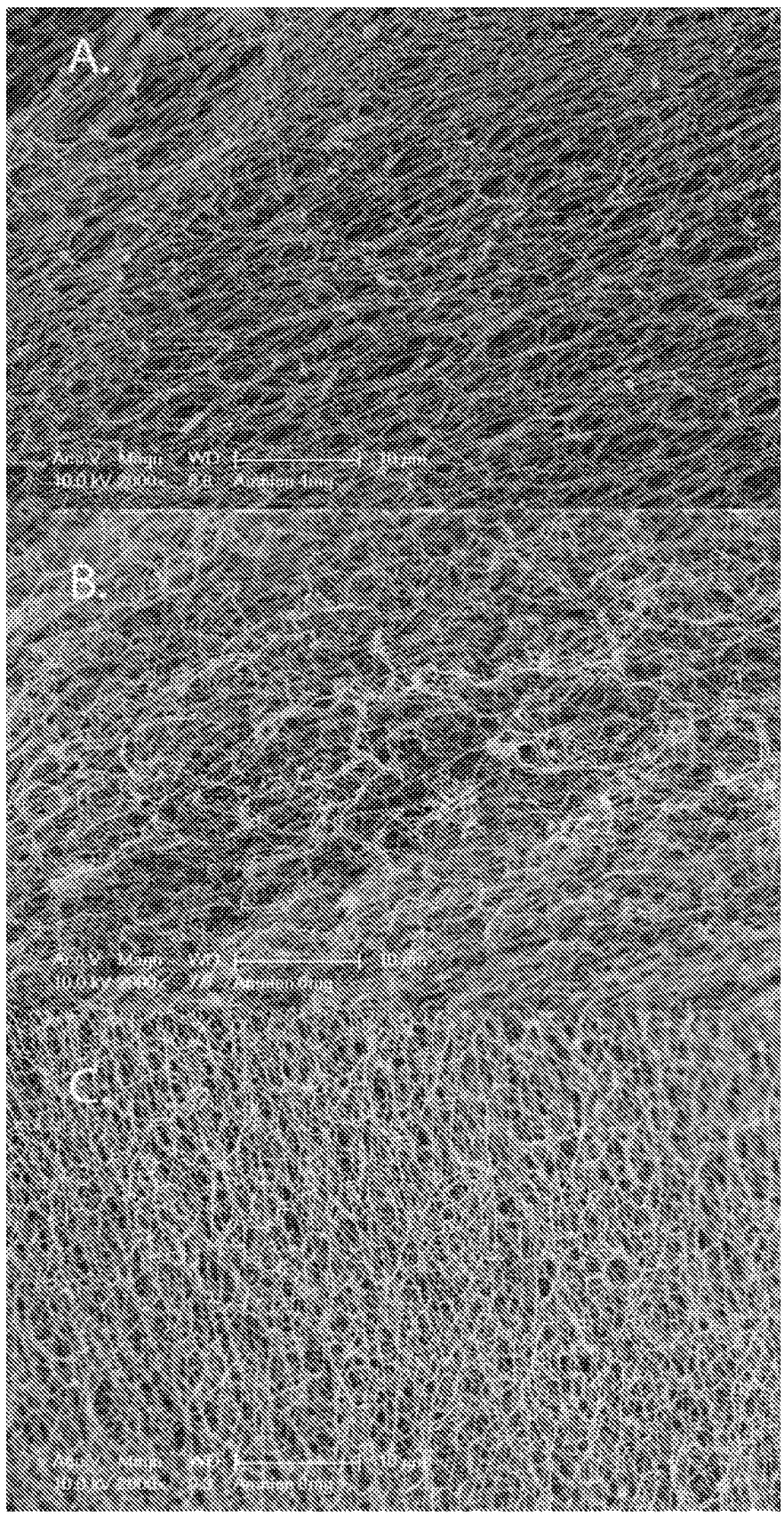
FIGS. 3A-3C show scanning electron microscopy images of amnion hydrogels.

These studies show a decrease in adhesion burden in animals treated with decellularized amniotic membrane and AM-ECM hydrogel compared to control animals. The application of the amniotic membrane can be optimized as demonstrated in FIG. 2B so that the injured surface of the peritoneal lining is completely covered by the membrane. Once this is optimized, additional in vivo studies with both the amniotic membrane sheet and AM-ECM hydrogel need to be carried out to determine if the suggested improvement in adhesion reduction is a significant finding and to determine the in vivo biodegradable capacity of the decellularized products.

Example 2

Current MSC therapies have limited clinical efficacy. For example they exhibit poor cellular survival upon delivery and limited integration after transplantation. In addition, after systemic delivery, many stem cells become entrapped in lungs and capillaries. Because MSCs re anchorage dependent cells, they are known to succumb to anoikis, or apoptosis induced by lack of correct cell/ECM attachment. Thus, it is necessary for cell to cell contact for attachment, and as a result, a biocompatible delivery vehicle is required to maintain cell viability and integration. In view of the above limitations of the art, collagen, fibrin, hyaluronic acid, matrigel compositions that are biocompatible and biodegradable are desired. The compositions as described herein provide flexibility of physical characteristics and can support cellular adhesion and can provide an extracellular matrix with structural similarities to natural tissue.

Current hydrogel compositions suffer from several limitations. For example, many are derived from non-human sources, such as mouse or bovine, and therefore can induce an undesired host immune response. They are expensive to manufacture and are often in limited supply. In contrast, the hydrogel compositions of this disclosure can be produced from enzymatically degraded tissues and will retain cell adhesion properties. They also can be used in cell culture as they provide compatible physiological properties.

In one aspect, this disclosure provides a human amnion derived hydrogel that is biocompatible. It is prepared from discarded term placenta.

Example 3

In-Vivo Cell Infiltration and Proinflammatory (M1) Macrophage Recruitment Histological and Immunofluorescence Examinations Amnion and collagen hydrogels at 10 mg/mL concentration were implanted into the back of Sprague Dawley rats by subcutaneous injection (each rat was injected with 2 ml amnion hydrogel on the left side and 2 ml collagen hydrogel on the right side in the back). After 14 days, the rats were sacrificed and the residual hydrogels with adjacent tissues were collected. The specimens were fixed in 10% formalin, washed in DI water and dehydrated in 30% sucrose before being embedded in O.C.T compound (Tissue Tek®), and sliced at 20 µm thickness using a cryostat. Hematoxylin and eosin (H&E) staining was employed to detect the residual bulk and the cell infiltration of amnion and collagen hydrogels. To identify the infiltration cell type, proinflammatory macrophage (M1 phenotype) marker CCR7 (Epitomics) was used. The sections were incubated with 10% (w/v) bovine serum albumin in PBS for 60 min to inhibit nonspecific binding of IgG. Then, the sections were incubated with rabbit anti-rat CCR7 antibody for 2 hour and detected with fluorescently labeled secondary antibody. The sections were counterstained with DAPI for 5 min to identify cell nuclei. All the sections were observed with a Carl Zeiss Axio Observer D1 inverted microscope. ImageJ software was employed to quantify CCR7+ cells in the tissue sections.

Results

Figure 11:
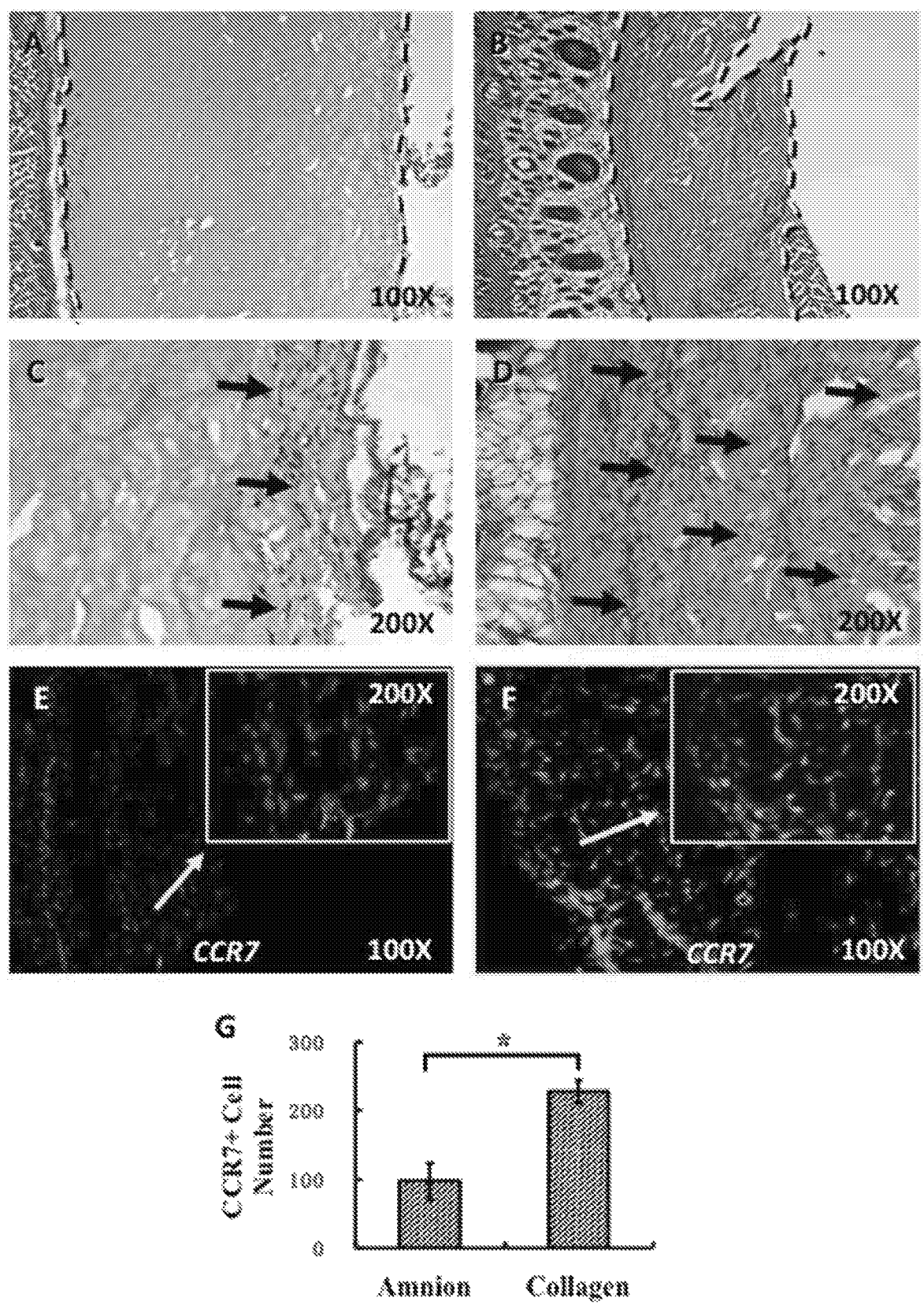
FIGS. 11A-11G show histological and immunofluorescence examination of in vivo application of the hydrogels in an animal model.

H&E staining examination showed the residual hydrogel (area between the two yellow imaginary lines, FIG. 11A) was thicker than collagen (FIG. 11B) and there was less cell infiltration (black arrow) in amnion hydrogel (FIG. 11C) than in collagen hydrogel (FIG. 11D). Immunofluorescence examination showed the infiltrated cells in amnion and collagen hydrogel were CCR7 positive (FIGS. 11E-11F). The density of CCR7+ cells in amnion hydrogel (FIG. 11E) was lower than in collagen hydrogel (FIG. 11F) and there was significant difference between them (p<0.01) (FIG. 11G). This indicated that the amnion hydrogel lower inflammatory reaction in vivo than the collagen hydrogel.

EQUIVALENTS

The disclosure illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosure embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

Ballios, B. G. et al. (2010). A hydrogelbased stem cell delivery system to treat retinal degenerative diseases. Biomaterials, 31(9), 2555-2564.

Beer, H. D. et al. (2000). Expression and function of keratinocyte growth factor and activin in skin morphogenesis and cutaneous wound repair. J Investig Dermatol Symp Proc, 5(1), 34-39. doi: 10.1046/j.1087-0024.2000.00009.x Bollini, S. et al. (2013). The regenerative role of the fetal and adult stem cell secretome. Journal of Clinical Medicine, 2(4), 302-327.

Caplan, A. I. & Dennis, J. E. (2006). Mesenchymal stem cells as trophic mediators. J Cell Biochem, 98(5), 1076-1084. doi: 10.1002/jcb.20886

Catelas, I. et al. (2006). Human mesenchymal stem cell proliferation and osteogenic differentiation in fibrin gels in vitro. Tissue Eng, 12(8), 2385-2396.

Clark, R. A. et al. (2007). Tissue engineering for cutaneous wounds. J Invest Dermatol, 127(5), 1018-1029. doi: 10.1038/sj.jid.5700715

Davis, H. E. et al. (2013). Enhancing osteoconductivity of fibrin gels with apatite-coated polymer microspheres. Tissue Eng Part A, 19(15-16), 1773-1782. doi: 10.1089/ten.TEA.2012.0288

DeQuach, J. A. et al. (2010). Simple and High Yielding Method for Preparing Tissue Specific Extracellular Matrix Coatings for Cell Culture. PLoS One, 5(9). doi: 10.1371/journal.pone.0013039

Diegelmann, R. F. & Evans, M. C. (2004). Wound healing: an overview of acute, fibrotic and delayed healing. Front Biosci, 9(1), 283-289.

Dominici, M. et al. (2006). Minimal criteria for defining multipotent mesenchymal stromal cells. The International Society for Cellular Therapy position statement. Cytotherapy, 8(4), 315-317. doi: 10.1080/14653240600855905

Donnelly, K. et al. (2010). A novel bioreactor for stimulating skeletal muscle in vitro. Tissue Eng Part C Methods, 16(4), 711-718. doi: 10.1089/ten.TEC.2009.0125

Elgharably, H. et al. (2013). A modified collagen gel enhances healing outcome in a preclinical swine model of excisional wounds. Wound Repair and Regeneration, 21(3), 473-481.

Firth, S. M. & Baxter, R. C. (2002). Cellular actions of the insulin-like growth factor binding proteins. Endocr Rev, 23(6), 824-854. doi: 10.1210/er.2001-0033

Gupta, S. K. et al. (1995). A potent inhibitor of endothelial cell proliferation is generated by proteolytic cleavage of the chemokine platelet factor 4. Proc Natl Acad Sci USA, 92(17), 7799-7803.

Hoeben, A. et al. (2004). Vascular endothelial growth factor and angiogenesis. Pharmacol Rev, 56(4), 549-580. doi: 10.1124/pr.56.4.3

Huang, N. F. et al. (2013). The modulation of endothelial cell morphology, function, and survival using anisotropic nanofibrillar collagen scaffolds. Biomaterials, 34(16), 4038-4047. doi: 10.1016/j.biomaterials.2013.02.036

Huh, D. et al. (2011). From 3D cell culture to organs-onchips. Trends in cell biology, 21(12), 745-754.

Karp, J. M. & Teo, G. S. L. (2009). Mesenchymal stem cell homing: the devil is in the details. Cell Stem Cell, 4(3), 206-216.

Kim, I. et al. (2013). Fibrin glue improves the therapeutic effect of MSCs by sustaining survival and paracrine function. Tissue Engineering Part A, 19(21-22), 2373-2381.

Li, A. et al. (2003). IL-8 directly enhanced endothelial cell survival, proliferation, and matrix metalloproteinases production and regulated angiogenesis. J Immunol, 170(6), 3369-3376.

Luttun, A. et al. (2002). Placental growth factor (PlGF) and its receptor Flt-1 (VEGFR-1): novel therapeutic targets for angiogenic disorders. Ann N Y Acad Sci, 979, 80-93.

Malek, A. & Bersinger, N. A. (2011). Human placental stem cells: biomedical potential and clinical relevance. J Stem Cells, 6(2), 75-92.

Man, D. et al. (2001). The use of autologous plateletrich plasma (platelet gel) and autologous platelet-poor plasma (fibrin glue) in cosmetic surgery. Plastic and reconstructive surgery, 107(1), 229-237; discussion 238-229.

Manuelpillai, U. et al. (2011). Amniotic membrane and amniotic cells: potential therapeutic tools to combat tissue inflammation and fibrosis? Placenta, 32 Suppl 4, S320-325. doi:10.1016/j.placenta.2011.04.010

Meierhenry, J. et al. (2015). Placenta as a Source of Stem Cells for Regenerative Medicine. Current Pathobiology Reports, 3(1), 9-16. doi: 10.1007/s40139-015-0070-6

Midwood, K. S. et al. (2004). Tissue repair and the dynamics of the extracellular matrix. The International Journal of Biochemistry & Cell Biology, 36(6), 1031-1037. doi: http://dx.doi.org/10.1016/j.biocel.2003.12.003

Murphy, M. B. et al. (2013). Mesenchymal stem cells: environmentally responsive therapeutics for regenerative medicine. Exp Mol Med, 45, e54. doi: 10.1038/emm.2013.94

Orban, J. M. et al. (2004). Crosslinking of collagen gels by transglutaminase. J Biomed Mater Res A, 68(4), 756-762. doi: 10.1002/jbm.a.20110

Phinney, D. G. & Prockop, D. J. (2007). Concise review: mesenchymal stem/multipotent stromal cells: the state of transdifferentiation and modes of tissue repair—current views. Stem Cells, 25(11), 2896-2902. doi: 10.1634/stemcells.2007-0637

Roy, R. et al. (2010). Processing of type I collagen gels using nonenzymatic glycation. J Biomed Mater Res A, 93(3), 843-851. doi: 10.1002/jbm.a.3223 I Slaughter, B. V. et al. (2009). Hydrogels in regenerative medicine. Advanced Materials, 21(32-33), 3307-3329.

van Hinsbergh, V. W. & Koolwijk, P. (2008). Endothelial sprouting and angiogenesis: matrix metalloproteinases in the lead. Cardiovasc Res, 78(2), 203-212. doi: 10.1093/cvr/cvm102

Wolf, M. T. et al. (2012). A hydrogel derived from decellularized dermal extracellular matrix. Biomaterials, 33(29), 7028-7038. doi:10.1016/j.biomaterials.2012.06.051

What is claimed is:

1. A hydrogel composition comprising:
   a powdered and freeze dried decellularized amniotic membrane (DCM), the amniotic membrane being decellularized using a method comprising:
      adding to the amniotic membrane about a 3% detergent solution comprising t-octylphenoxypolyethoxyethanol solution to lyse the cells,
      rinsing with de-ionized water to remove the detergent solution,
      adding about a 4% sodium deoxycholic acid solution to further decellularize the membrane,
      rinsing with de-ionized water to remove the acid solution,
      adding a solution of about 0.1% peracetic acid/4% ethanol solution to remove residual nucleic acids,
      rinsing with a composition comprising phosphate buffered saline and subsequently de-ionized water, and
      removing excess water;
   stem cells;
   a non-cytotoxic cross-linking agent; and
   a carrier comprising buffered saline.

2. The hydrogel composition of claim 1, wherein the DCM is processed by lyophilization and micronized into powder.

3. The hydrogel composition of claim 1, wherein the DCM is derived from placenta isolated from a human, an ovine, a porcine, a bovine, an equine, a feline, a canine or a murine.

4. The hydrogel composition of claim 1, wherein the carrier is a pharmaceutically acceptable carrier comprising buffered saline.

5. The hydrogel composition of claim 4, wherein the pharmaceutically acceptable carrier further comprises deionized water or a collagen-based product.

6. The hydrogel composition of claim 1, wherein the stem cells comprise mesenchymal stem cells, bone marrow stem cells, or placental derived mesenchymal stem cells (PMSCs).

7. The hydrogel composition of claim 1, further comprising pepsin.

8. The hydrogel composition of claim 1, wherein the hydrogel composition is a topical gel.

9. The hydrogel composition of claim 1, further comprising one or more antibiotics, anti-inflammatory agents or growth factors.

10. A kit comprising the hydrogel composition of claim 1.

11. The kit of claim 10, further comprising instructions for use.

12. The kit of claim 10, further comprising instructions for administration by one or more of topical, intraperitoneal, implantation, local, or systemic administration route.

13. A method to culture a cell, comprising mixing an exogenous cell with the hydrogel composition of claim 1, and culturing the exogenous cell under conditions that favor growth and expansion of the exogenous cell.

14. The method of claim 13, wherein the mixing is in vitro or in vivo.

15. The method of claim 13, wherein the exogenous cell is selected from the group consisting of a stem cell and a mesenchymal stem cell.

16. A method to treat a wound, comprising administering to a subject in need thereof, an effective amount of the hydrogel composition of claim 1, thereby treating the wound.

17. A method for regulating, treating or preventing inflammation in a subject in need thereof, comprising administering to the subject in need thereof, an effective amount of the hydrogel composition of claim 1, thereby regulating, treating or preventing inflammation.

18. A method for treating or preventing adhesion or scar formation in a subject in need thereof, comprising administering to the subject in need thereof, an effective amount of the hydrogel composition of claim 1, thereby treating or preventing adhesion or scar formation.

19. A method to treat spinal cord injury or Spina *bifida*, comprising administering to a subject in need thereof an effective amount of the hydrogel composition of claim 1, thereby treating spinal cord injury or Spina *bifida*.

20. A method to promote vascularization in a subject in need thereof, comprising administering to the subject in need thereof, an effective amount of the hydrogel composition of claim 1, thereby promoting vascularization in the subject.

21. The method of any one of claims 16 to 18, wherein administration comprises one or more of topical, intraperitoneal, implantation, local, or systemic.

22. The method of claim 21, wherein the stem cells are autologous or allogeneic to the subject being treated.

23. The method of any one of claims 16 to 20, wherein the subject is a human, a bovine, an equine, a feline, a canine or a murine.

24. The method of any one of claims 16 to 20, wherein the composition further comprises one or more antibiotics, anti-inflammatory agents or growth factors.

25. A method to promote neural tissue repair or regeneration, comprising administering to a subject in need thereof an effective amount of the hydrogel composition of claim 1, thereby promoting neural tissue repair or regeneration.

* * * * *